(12) United States Patent
Jefford et al.

(10) Patent No.: US 9,763,915 B2
(45) Date of Patent: Sep. 19, 2017

(54) ADJUVANTS IN ANTI-CANCER CHEMOTHERAPY

(71) Applicants: Charles William Jefford, Bogis-Bossey (CH); Daniel Hoessli, Geneva (CH)

(72) Inventors: Charles William Jefford, Bogis-Bossey (CH); Daniel Hoessli, Geneva (CH)

(73) Assignee: PharmOxaco SáRL (CH)

( * ) Notice: Subject to any disclaimer, the term of this patent is extended or adjusted under 35 U.S.C. 154(b) by 0 days.

(21) Appl. No.: 15/041,198

(22) Filed: Feb. 11, 2016

(65) Prior Publication Data

US 2016/0158193 A1 Jun. 9, 2016

Related U.S. Application Data

(63) Continuation of application No. PCT/GB2014/052392, filed on Aug. 5, 2014.

(30) Foreign Application Priority Data

Aug. 15, 2013 (GB) .................................. 1314639.4

(51) Int. Cl.
*A61K 31/357* (2006.01)

(52) U.S. Cl.
CPC .................................. *A61K 31/357* (2013.01)

(58) Field of Classification Search
CPC .................................................... A61K 31/357
USPC ........................................................ 514/452
See application file for complete search history.

(56) References Cited

U.S. PATENT DOCUMENTS 5,559,145 A 9/1996 Jefford
2005/0256184 A1 11/2005 O'Neill et al.

FOREIGN PATENT DOCUMENTS

| EP | 0286316 A1 | 10/1988 |
|---|---|---|
| WO | WO-2006/016903 A2 | 2/2006 |
| WO | WO-2013/177420 A2 | 11/2013 |

OTHER PUBLICATIONS

Vargas et al, Scandinavian Journal of Immunology, published online 2013, pp. 130-139.*
Arora and Scholar, "Role of Tyrosine Kinase Inhibitors in Cancer Therapy," Perspectives in Pharmacology (2005), vol. 315 (3), pp. 971-979.*
Peters et al, Ann. Trop. Med. Parasitol., 1993, 87, pp. 9-16.*
Efferth et al., "Combination treatment of glioblastoma multiforme cell lines with the anti-malarial artesunate and the epidermal growth factor receptor tyrosine kinase inhibitor OSI-774," *Biochem. Pharmacol.*, 67(9):1689-1700 (2004).
Efferth, "Mechanistic perspectives for 1,2,4-trioxanes in anti-cancer therapy," *Drug Resist. Updates,* Churchill Livingston, Edinburgh, GB, 8(1-2):85-97 (2005).
Jefford et al., "51. Synthesis, Structure, and Antimalarial Activity of Some Enantiomerically Pure, cis-Fused Cyclopenteno-1,2,4-trioxanes-I 21 1 Geneva 4 and Ignacio Manzanares Pharma Mar SA, E-28760 Tres Cantos (Madrid)," Helvetica Chimica Acta, [retrieved from the Internet Sep. 5, 2014: URL:http://onlinelibrary.wiley.com/store/10.1002/hlca.19950780312/asset/19950780312_ftp.pdf?v=1&t=hzpi25nh&s=8ef88366744a3f21175edb9fbb17338746340b87 (1995).
International Search Report issued Nov. 17, 2014 in PCT/GB2014/052392.
Search Report issued Jan. 28, 2014 in GB 1314639.4.

* cited by examiner

*Primary Examiner* — Kathrien Cruz
*Assistant Examiner* — Janet L Coppins
(74) *Attorney, Agent, or Firm* — McCarter & English, LLP; Yu Lu; Wei Song

(57) ABSTRACT

The present invention provides a 1,2,4-trioxane or a pharmaceutically acceptable salt, ester, solvate, tautomer or stereoisomer thereof for use as an adjuvant for a tyrosine kinase inhibitor to enhance the activity of said tyrosine kinase inhibitor in a method for the treatment of a patient suffering from cancer, a pharmaceutical composition comprising a tyrosine kinase inhibitor as an active ingredient and said 1,2,4-trioxane adjuvant or a pharmaceutically acceptable salt, ester, solvate, tautomer or stereoisomer thereof in an amount sufficient to enhance the activity of the tyrosine kinase inhibitor, preferably for use in a method for the treatment of cancer.

38 Claims, No Drawings

ADJUVANTS IN ANTI-CANCER CHEMOTHERAPY

REFERENCE TO RELATED APPLICATIONS

This application is a continuation application of international patent application no. PCT/GB2014/052392, filed on Aug. 5, 2014; which claims priority from United Kingdom patent application no. 1314639.4, filed on Aug. 15, 2013, the entire contents of each of which are incorporated herein by reference in its entirety.

FIELD OF THE INVENTION

The present invention relates to adjuvant compounds for use in tyrosine kinase inhibitor therapy for the treatment of cancer, to compositions comprising a tyrosine kinase inhibitor as an active ingredient and an adjuvant compound in an amount sufficient to enhance the activity of the tyrosine kinase inhibitor and the use thereof in a method of treatment of cancer and to a method for the treatment of cancer comprising administering to a patient in need thereof a tyrosine kinase inhibitor as an active ingredient and an adjuvant compound in an amount sufficient to enhance the activity of the tyrosine kinase inhibitor.

BACKGROUND OF THE INVENTION

Tyrosine kinase inhibitors (TKIs) have become the drugs of choice for treating a variety of human cancers (A. Arora and E. M. Scholar, *J. Pharmacol. Experimtl. Therapeutics,* 2005, 315, 971-979; A. Opar, *Nature Rev. Drug Discovery,* 2012, 11, 819-820). These drugs were developed in the late 1990s from the initial finding that 2-phenylaminopyrimidine derivatives could inhibit the action of proteins driving cell proliferation and resisting apoptosis (programmed cell death) by blocking the active site for phosphorylation of tyrosine by ATP (adenosine triphosphate) (P. Yaish, A. Gazit, C. Gilon, A. Levitzki. *Science* 1988, 242, 933-935; B. J. Drucker, *Blood*, 2008, 112, 4808-4817).

The pharmaceutical industry has produced an array of such derivatives for clinical use, for example, imatinib, nilotinib, bafetinib, erlotinib, lapatinib, and dasatinib, which display specific binding characteristics for different kinases. Derivatives bearing the 2-phenylaminopyrimidine motif are not the only examples of tyrosine kinase inhibitors (TKIs) that have activity in treating human cancers. Derivatives of indole, quinoline, and pyridine have also been developed as TKIs, for example, motesanib, sunitinib, carbozantinib, gefitinib, and vatalanib. Natural products such as emodin (an anthraquinone), geneistein (an isoflavone), radiciol (an epoxyresorcinol) also display inhibitory activity against tyrosine kinases.

Kinases driving proliferation in normal and cancer cells fall into two categories: receptor and non-receptor tyrosine kinases. Receptor kinases are the transmembrane proteins serving as receptors for growth factors that normal cells utilize to respond to environmental cues. Non-receptor kinases are essentially involved in proliferation and apoptosis resistance. Cancer cells can therefore grow without depending on extracellular factors. No external stimulation is required for carrying out phosphorylation of tyrosine by ATP. In practice, the proliferation of cancer cells can be selectively blocked by a variety of TKIs (D. S Krause and R. A. Van Etten, *N. Eng. J. Med.* 2005, 353, 172-187). How this happens is not precisely known. Examples include epidermal growth factor receptors (EGFR), platelet derived growth factors (PDGF), bcr-abl, c-KIT kinases, FLT kinases, platelet derived growth factors (PDGFR), vascular endothelial growth factors (VEGFR) and Src-family non-receptor kinases.

To be clinically useful, a tyrosine kinase inhibitor needs to be administered at micromolar concentrations (0.1 to 1.0 µM). However, only a few tyrosine kinase inhibitors are effective at such low concentrations.

There is a clear clinical need to improve the activity of weak tyrosine kinase inhibitors so that they can be administered to patients in micromolar, clinically useful doses, thus enabling them to be developed as potentially useful cancer medications.

SUMMARY OF THE INVENTION

It has been surprisingly found that certain 1,2,4-trioxanes derivatives show activity as adjuvants to proprietary tyrosine kinase inhibitors and naturally occurring tyrosine kinase inhibitors by significantly enhancing their efficacy as clinical anti-cancer therapeutic agents.

Specifically, it has been discovered that certain cis-fused cyclopenteno-1,2,4-trioxanes, previously developed as antimalarials (W. Peters, B. L. Robinson, J. C. Rossier, D. Misra, and C. W. Jefford, *Ann. Trop. Med. Parasitol.,* 1993, 87, 9-16), which are not chemically related to the N-heterocyclic TKIs and which show no antitumor activity, can be deployed as adjuvants to substantially augment the effectiveness of proprietary pharmaceutical TKIs and naturally occurring TKIs. These previously reported synthetic derivatives of 1,2,4-trioxane exhibit new, pharmaceutically useful properties, in particular, the enhancement of the effectiveness of certain tyrosine kinase inhibitors when used in combination with them as an adjuvant.

Thus, in a first aspect of the present invention there is provided a 1,2,4-trioxane of formula (I) or a pharmaceutically acceptable salt, ester, solvate, tautomer or stereoisomer thereof for use as an adjuvant for a tyrosine kinase inhibitor to enhance the activity of said tyrosine kinase inhibitor in a method for the treatment of a patient suffering from cancer:

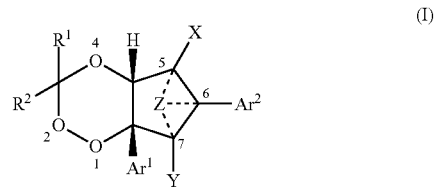

(I)

wherein
each of substituents $R^1$ and $R^2$, which can be the same or different, represents a linear or branched alkyl group having from 1 to 12 carbon atoms, a linear or branched alkenyl group having from 2 to 12 carbon atoms or a linear or branched alkynyl group having from 2 to 12 carbon atoms, each of which can optionally be substituted with one or more substituents chosen from substituents $R^x$, or $R^1$ and $R^2$ taken together with the carbon atom to which they are attached can form an alicyclic group having from 3 to 8 carbon atoms which may optionally be interrupted by one or more oxygen, sulphur or nitrogen atoms, wherein said alicyclic group may optionally be substituted with one or more substituents chosen from substituents $R^x$;

each of the substituents Ar¹ and Ar², which can be the same or different, represents an aromatic group selected from aryl groups having from 6 to 18 carbon atoms in one or more rings, and 5- to 14-membered heteroaryl groups having one or more rings, wherein said aryl group or said heteroaryl group may optionally be substituted with one or more substituents chosen from substituents $R^x$;

each of the substituents X and Y, which can be the same or different, represents a hydrogen atom or a functional group that contains oxygen, sulphur or nitrogen;

the substituent Z represents an epoxide oxygen atom attached to the 5,6 or 6,7 positions or a pair of electrons forming a double bond at the 5,6 or 6,7 positions; and said substituents $R^x$ are selected from the group consisting of $C_1$-$C_{12}$ alkyl groups which may be optionally substituted with at least one group $R^y$, $C_2$-$C_{12}$ alkenyl groups which may be optionally substituted with at least one group $R^y$, $C_2$-$C_{12}$ alkynyl groups which may be optionally substituted with at least one group $R^y$, halogen atoms, oxo groups, thio groups, cyano groups, nitro groups, $OR^y$, $OCOR^y$, $OCOOR^y$, $COR^y$, $COOR^y$, $OCONR^yR^z$, $CONR^yR^z$, $S(O)R^y$, $SO_2R^y$, $P(O)(R^y)OR^z$, $NR^yR^z$, $NR^yCOR^z$, $NR^yC(=O)NR^yR^z$, $NR^yC(=NR^y)NR^yR^z$, aryl groups having from 6 to 18 carbon atoms in one or more rings which may optionally be substituted with one or more substituents which may be the same or different selected from the group consisting of $R^y$, $OR^y$, $OCOR^y$, $OCOOR^y$, $NR^yR^z$, $NR^yCOR^z$ and $NR^yC(=NR^y)NR^yR^z$, aralkyl groups comprising an alkyl group having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R^y$, and where there is more than one optional substituent on any given group the optional substituents $R^y$ may be the same or different;

each $R^y$ and $R^z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl groups comprising a $C_1$-$C_{12}$ alkyl group that is substituted with a 5- to 14-membered unsaturated or saturated heterocyclic group having one or more rings and comprising at least one oxygen, nitrogen or sulphur atom in said ring(s).

As we shall explain and exemplify below, the use of a 1,2,4-trioxane of formula (I) or a pharmaceutically acceptable salt, ester, solvate, tautomer or stereoisomer thereof as an adjuvant for a tyrosine kinase inhibitor enhances the activity of a tyrosine kinase inhibitor in a method for the treatment of a patient suffering from cancer compared to the activity of the same amount of said tyrosine kinase inhibitor used alone in said method of treatment. The increase in activity of the tyrosine kinase activity through use of the 1,2,4-trioxane adjuvant means that the tyrosine kinase inhibitors can now become clinically effective antitumor agents, as it is possible to use them at a clinically useful micromolar dose (i.e. the increase in activity as a result of the use of the 1,2,4-trioxane adjuvant leads to a lower effective dose of the tyrosine kinase inhibitor being required).

We have discovered that the 1,2,4-trioxanes of formula (I) and pharmaceutically acceptable salts, esters, solvates, tautomers and stereoisomers thereof of the present invention, markedly improve the efficacy of some typical, clinically available tyrosine kinase inhibitors, by attaining a similar anti-cancer activity at 10-fold lower concentrations of the tyrosine kinase inhibitor. Without wishing to be bound by theory, it is believed that the synthetic 1,2,4-trioxanes of formula (I) of the present invention, which are liposoluble, act in the cells plasma membrane where the oncogenic proteins lie and where the tyrosine kinases also operate. We therefore believe that it is possible that these synthetic trioxanes are thus indirectly influencing the interaction of the tyrosine kinase inhibitors with the tyrosine kinase oncogenic protein.

For both lymphoma and human breast cancer cell lines, for example, it has been found that those of high proliferative capacity can be made significantly more sensitive (up to 4-fold) to tyrosine kinase inhibitors by use in combination with preferred synthetic trioxanes of the present invention as adjuvant. Moreover, highly malignant cancers, which are more difficult to treat, are more susceptible to the trioxane adjuvant effect than those of low malignancy.

The main advantage of adjuvant therapies of the kind we propose with synthetic trioxanes is that tyrosine kinase inhibitors can be made effective at much lower concentrations, thus considerably decreasing the impact of side effects and the cost of treatment. The therapeutic index of other less active tyrosine kinase inhibitors, presently clinically unusable, can be improved by combination with an active synthetic trioxane.

In a second aspect of the present invention there is provided a pharmaceutical composition comprising a tyrosine kinase inhibitor as an active ingredient and a 1,2,4-trioxane of formula (I) adjuvant or a pharmaceutically acceptable salt, ester, solvate, tautomer or stereoisomer thereof in an amount sufficient to enhance the activity of the tyrosine kinase inhibitor, and a pharmaceutically acceptable carrier:

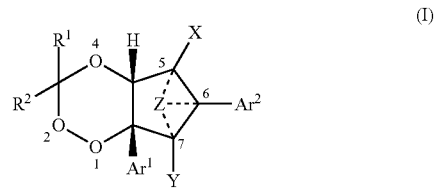

(I)

wherein each of substituents R¹ and R², which can be the same or different, represents a linear or branched alkyl group having from 1 to 12 carbon atoms, a linear or branched alkenyl group having from 2 to 12 carbon atoms or a linear or branched alkynyl group having from 2 to 12 carbon atoms, each of which can optionally be substituted with one or more substituents chosen from substituents $R^x$, or R¹ and R² taken together with the carbon atom to which they are attached can form an alicyclic group having from 3 to 8 carbon atoms which may optionally be interrupted by one or more oxygen, sulphur or nitrogen atoms, wherein said alicyclic group may optionally be substituted with one or more substituents chosen from substituents $R^x$;

each of the substituents $Ar^1$ and $Ar^2$, which can be the same or different, represents an aromatic group selected from aryl groups having from 6 to 18 carbon atoms in one or more rings, and 5- to 14-membered heteroaryl groups having one or more rings, wherein said aryl group or said heteroaryl group may optionally be substituted with one or more substituents chosen from substituents $R^x$;

each of the substituents X and Y, which can be the same or different, represents a hydrogen atom or a functional group that contains oxygen, sulphur or nitrogen;

the substituent Z represents an epoxide oxygen atom attached to the 5,6 or 6,7 positions or a pair of electrons forming a double bond at the 5,6 or 6,7 positions; and said substituents RX are selected from the group consisting of $C_1$-$C_{12}$ alkyl groups which may be optionally substituted with at least one group $R^y$, $C_2$-$C_{12}$ alkenyl groups which may be optionally substituted with at least one group $R^y$, $C_2$-$C_{12}$ alkynyl groups which may be optionally substituted with at least one group $R^y$, halogen atoms, thio groups, cyano groups, nitro groups, oxo groups, $OR^y$, $OCOR^y$, $OCOOR^y$, $COR^y$, $COOR^y$, $OCONR^yR^z$, $CONR^yR^z$, $S(O)R^y$, $SO_2R^y$, $P(O)(R^y)OR^z$, $NR^yR^z$, $NR^yCOR^z$, $NR^yC(=O)NR^yR^z$, $NR^yC(=NR^y)NR^yR^z$, aryl groups having from 6 to 18 carbon atoms in one or more rings which may optionally be substituted with one or more substituents which may be the same or different selected from the group consisting of $R^y$, $OR^y$, $OCOR^y$, $OCOOR^y$, $NR^yR^z$, $NR^yCOR^z$ and $NR^yC(=NR^y)NR^yR^z$, aralkyl groups comprising an alkyl group having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R^y$, and where there is more than one optional substituent on any given group the optional substituents $R^y$ may be the same or different;

each $R^y$ and $R^z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl groups comprising a $C_1$-$C_{12}$ alkyl group that is substituted with a 5- to 14-membered unsaturated or saturated heterocyclic group having one or more rings and comprising at least one oxygen, nitrogen or sulphur atom in said ring(s).

In a third aspect of the present invention, there is provided a pharmaceutical composition comprising a tyrosine kinase inhibitor as an active ingredient and a 1,2,4-trioxane of formula (I) adjuvant as defined above or a pharmaceutically acceptable salt, ester, solvate, tautomer or stereoisomer thereof to enhance the activity of the tyrosine kinase inhibitor, and a pharmaceutically acceptable carrier, for use in a method for the treatment of cancer.

In a fourth aspect of the present invention, there is provided a kit comprising a tyrosine kinase inhibitor as an active ingredient and a 1,2,4-trioxane of formula (I) adjuvant as defined above or a pharmaceutically acceptable salt, ester, solvate, tautomer or stereoisomer thereof in an amount sufficient to enhance the activity of the tyrosine kinase inhibitor.

In a fifth aspect of the present invention, there is provided a method for the treatment of cancer comprising administering to a patient in need thereof a tyrosine kinase inhibitor as an active ingredient and a 1,2,4-trioxane of formula (I) adjuvant or a pharmaceutically acceptable salt, ester, solvate, tautomer or stereoisomer thereof as defined above in an amount sufficient to enhance the activity of the tyrosine kinase inhibitor.

In a sixth aspect of the present invention, there is provided use of a 1,2,4-trioxane of formula (I) adjuvant or a pharmaceutically acceptable salt, ester, solvate, tautomer or stereoisomer thereof as defined above in the manufacture of a medicament further comprising a tyrosine kinase inhibitor as an active ingredient for the treatment of cancer.

DETAILED DESCRIPTION OF PREFERRED EMBODIMENTS OF THE INVENTION

In the compounds of the present invention the alkyl groups in the definitions of $R^1$, $R^2$, $R^x$, $R^y$ and $R^z$ are straight chain or branched alkyl chain groups having from 1 to 12 carbon atoms, and they are preferably an alkyl group having from 1 to 6 carbon atoms, more preferably a methyl group, an ethyl group, an i-propyl group or a t-butyl group, and most preferably a methyl group. In $R^{y'}$, $R^{z'}$ and $R^{y''}$ the alkyl groups may be straight chain or branched alkyl chain groups having from 1 to 6 carbon atoms.

In the compounds of the present invention the alkenyl groups in the definitions of $R^1$, $R^2$ and $R^x$ are branched or unbranched, and may have one or more double bonds and from 2 to 12 carbon atoms. Preferably, they have from 2 to 6 carbon atoms, and more preferably they are vinyl groups.

In the compounds of the present invention the alkynyl groups in the definitions of $R^1$, $R^2$ and $R^x$ are branched or unbranched, and may have one or more double bonds and from 2 to 12 carbon atoms. Preferably, they have from 2 to 6 carbon atoms, and more preferably they are ethynyl groups.

In the compounds of the present invention the alicyclic groups which may be formed by $R^1$ and $R^2$ together with the carbon atom to which they are attached are alicyclic groups selected from a cycloalkane group having from 3 to 8 carbon atoms and a cycloalkene group having from 3 to 8 carbon atoms and one or more double bonds, wherein said cycloalkane and cycloalkene groups may optionally be interrupted by one or more oxygen, sulphur or nitrogen atoms. Preferably, the alicyclic group is a cycloalkane group having from 4 to 7 carbon atoms or a cycloalkene group having from 5 to 7 carbon atoms, wherein said cycloalkane or cycloalkane groups may be interrupted by 1 or 2 oxygen, nitrogen or sulphur atoms, and most preferably it is a cyclopentane group, a cyclohexane group, a cyclohexene group or a tetrahydropyranyl group.

In the compounds of the present invention the aryl groups in the definitions of $Ar^1$, $Ar^2$ and $R^x$ are single or multiple ring compounds that contain separate and/or fused aryl groups and have from 6 to 18 ring atoms and are optionally substituted. Typical aryl groups contain from 1 to 3 separated or fused rings. Preferably the aryl groups contain from 6 to 12 carbon ring atoms. Particularly preferred aryl groups include phenyl, naphthyl, biphenyl, phenanthryl and anthryl, and most preferably phenyl.

In the compounds of the present invention the heteroaryl groups in the definitions of $Ar^1$ and $Ar^2$ are 5- to 14-membered heteroaromatic groups, comprising at least one oxygen, nitrogen or sulphur atom in said ring(s), and said groups containing from 1 to 3 separated or fused rings. Preferably the heteroaryl groups contain from 5 to 8 ring atoms. Suitable heteroaryl groups in the compounds of the present invention contain one, two or three heteroatoms selected from N, O or S atoms and include, for example, quinolyl including 8-quinolyl, isoquinolyl, coumarinyl including 8-coumarinyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl, and most preferably a pyridine group, a pyrimidinyl group, a furyl group, a pyrrolyl group and a thienyl group.

In the compounds of the present invention the functional group that contains oxygen in substituents X and Y may be a substituent selected from the group consisting of an oxo group, a hydroxyl group, a hydroperoxy group, an alkoxy group having from 1 to 6 carbon atoms, a group of formula $OCOR^y$ wherein $R^y$ is an alkyl group having from 1 to 6 carbon atoms and a group of formula $OCOOR^y$ wherein $R^y$ is an alkyl group having from 1 to 6 carbon atoms, preferably an oxo group, a hydroxyl group, a hydroperoxy group and a group of formula $OCOOR^y$ wherein $R^y$ is an alkyl group having from 1 to 6 carbon atoms.

In the compounds of the present invention the functional group that contains nitrogen in substituents X and Y may be a substituent selected from the group consisting of a group of formula $=NR^y$ wherein $R^y$ is a hydrogen atom or an alkyl group having from 1 to 6 carbon atoms, a group of formula $NR^yR^z$ wherein each of $R^y$ and $R^z$, which can be the same or different, can be a hydrogen atom or an alkyl group having from 1 to 6 carbon atoms, a group of formula $NR^yCOR^z$, wherein each of $R^y$ and $R^z$ can the same or different and is hydrogen or an alkyl group having from 1 to 6 carbon atoms and a nitro group, preferably an amino group or an imine group.

In the compounds of the present invention the functional group that contains sulphur in substituents X and Y may be a substituent selected from the group consisting of a thione group, a thiol group, a disulfane group, a group of formula $S(O)R^y$ wherein $R^y$ is a hydrogen atom or an alkyl group having from 1 to 6 carbon atoms and a group of formula $SO_2R$ wherein $R^y$ is a hydrogen atom or an alkyl group having from 1 to 6 carbon atoms, preferably a thione group and a thiol group.

The halogen atoms in the definitions of $R^x$, $R^y$ and $R^z$ include F, Cl, Br and I, preferably F and Cl.

The aralkyl groups in the definitions of $R^x$, $R^y$ and $R^z$ comprise an alkyl group having from 1 to 12 carbon atoms as defined and exemplified above which is substituted with one or more aryl groups having from 6 to 18 carbon atoms as defined and exemplified above. Preferred examples include optionally substituted benzyl, optionally substituted phenylethyl and optionally substituted naphthylmethyl.

In the compounds of the present invention, the aralkyloxy groups in the definition of $R^x$ comprise an alkoxy group having from 1 to 12 carbon atoms as defined and exemplified above which is substituted with one or more aryl groups having from 6 to 18 carbon atoms as defined and exemplified above. Preferably, the alkoxy moiety has from 1 to 6 carbon atoms and the aryl group contains from 6 to about 12 carbon ring atoms, and most preferably the aralkyloxy group is optionally substituted benzyloxy, optionally substituted phenylethoxy and optionally substituted naphthylmethoxy.

In the compounds of the present invention, the heterocyclic groups in the definition of $R^x$ comprises a heterocyclic groups having from 5 to 14 ring carbon atoms, having from 1 to 3 rings, and wherein the heterocyclic group can be aromatic, partially saturated or fully saturated. Preferably, the heterocyclic groups comprise from 5 to 10 ring atoms in 1 or 2 rings. More preferably, the heterocyclic groups comprise a heterocyclic group selected from the group consisting of pyrrolidinyl, imidazolidinyl, piperidinyl, piperazinyl, morpholinyl, tetrahydrofuranyl, thioanyl, oxanyl, thianyl, 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl and benzimidazole.

In the compounds of the present invention, the heterocycloalkyl groups in the definitions of $R^y$ and $R^z$ comprise an alkyl group having from 1 to 12 carbon atoms as defined and exemplified above which is substituted with one or more heterocyclyl groups having from 5 to 14 ring carbon atoms, in from 1 to 3 rings, and wherein the heterocyclyl group can be aromatic, partially saturated or fully saturated. Preferably, the heterocycloalkyl groups comprise an alkyl group having from 1 to 6 carbon atoms which is substituted with a heterocyclyl group having from 5 to 8 ring atoms in 1 or 2 rings. More preferably, the heterocycloalkyl groups comprise a methyl or ethyl group which is substituted with a heterocyclyl group selected from the group consisting of pyrrolidinyl, imidazolidinyl, piperidinyl, piperazinyl, morpholinyl, tetrahydrofuranyl, thioanyl, oxanyl, thianyl, 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl and benzimidazole.

The term "adjuvant" in the present invention means a compound A which, when used in combination with another compound B, increases the activity of that compound B when compared to the activity of the same amount of compound B when used alone. Specifically, in the present invention the 1,2,4 trioxanes of formula (I) or a pharmaceutically acceptable salt, ester, solvate, tautomer or stereoisomer thereof act as an adjuvant for tyrosine kinase inhibitors by increasing their activity as clinical anti-cancer therapeutic agents.

The term "a pharmaceutically acceptable salt, ester, solvate, tautomer or stereoisomer" of the 1,2,4-trioxanes of formula (I) of the present invention refers to any pharmaceutically acceptable salt, ester, solvate, hydrate or stereosiomeric form or any other compound which, upon administration to the patient is capable of providing a compound as described herein, whether directly or indirectly. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound, which may contain a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The 1,2,4-trioxanes of formula (I) of the present invention may be in crystalline form either as free compounds or as solvates (e.g. hydrates) and it is intended that both forms are within the scope of the present invention. Methods of solvation are generally known within the art.

Any compound that is a prodrug of the 1,2,4-trioxanes of formula (I) of the present invention is within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester derivative. Many suitable prodrugs are well-known to the person in the art and can be found, for example, in Burger "Medicinal Chemistry and Drug Discovery 6$^{th}$ ed. (Donald J. Abraham ed., 2001, Wiley) and "Design and Applications of Prodrugs" (H. Bundgaard ed., 1985, Harwood Academic Publishers), the contents of which are incorporated herein by reference.

In relations to the 1,2,4-trioxanes of formula (I) of the present invention, the pharmacologically acceptable esters are not particularly restricted, and can be selected by a person with an ordinary skill in the art. In the case of said esters, it is preferable that such esters can be cleaved by a biological process such as hydrolysis in vivo. The group constituting the said esters (the group shown as R when the esters thereof are expressed as —COOR) can be, for example, a $C_1$-$C_4$ alkoxy $C_1$-$C_4$ alkyl group such as methoxyethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, propoxymethyl, isopropoxymethyl, butoxymethyl or t-butoxymethyl; a $C_1$-$C_4$ alkoxylated $C_1$-$C_4$ alkoxy $C_1$-$C_4$ alkyl group such as 2-methoxyethoxymethyl; a $C_6$-$C_{10}$ aryloxy $C_1$-$C_4$ alkyl group such as phenoxymethyl; a halogenated $C_1$-$C_4$ alkoxy $C_1$-$C_4$ alkyl group such as 2,2,2-trichloroethoxymethyl or bis(2-chloroethoxy)methyl; a $C_1$-$C_4$ alkoxycarbonyl $C_1$-$C_4$ alkyl group such as methoxycarbonylmethyl; a cyano $C_1$-$C_4$ alkyl group such as cyanomethyl or 2-cyanoethyl; a $C_1$-$C_4$ alkylthiomethyl group such as methylthiomethyl or ethylthiomethyl; a $C_6$-$C_{10}$ arylthiomethyl group such as phenylthiomethyl or naphthylthiomethyl; a $C_1$-$C_4$ alkylsulfonyl $C_1$-$C_4$ lower alkyl group, which may be optionally substituted with a halogen atom(s) such as 2-methanesulfonylethyl or 2-trifluoromethanesulfonylethyl; a $C_6$-$C_{10}$ arylsulfonyl $C_1$-$C_4$ alkyl group such as 2-benzenesulfonylethyl or 2-toluenesulfonylethyl; a $C_1$-$C_7$ aliphatic acyloxy $C_1$-$C_4$ alkyl group such as formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl or 1-pivaloyloxyhexyl; a $C_5$-$C_6$ cycloalkylcarbonyloxy $C_1$-$C_4$ alkyl group such as cyclopentylcarbonyloxymethyl, cyclohexylcarbonyloxymethyl, 1-cyclopentylcarbonyloxyethyl, 1-cyclohexylcarbonyloxyethyl, 1-cyclopentylcarbonyloxypropyl, 1-cyclohexylcarbonyloxypropyl, 1-cyclopentylcarbonyloxybutyl or 1-cyclohexylcarbonyloxybutyl; a $C_6$-$C_{10}$ arylcarbonyloxy $C_1$-$C_4$ alkyl group such as benzoyloxymethyl; a $C_1$-$C_6$ alkoxycarbonyloxy $C_1$-$C_4$ alkyl group such as methoxycarbonyloxymethyl, 1-(methoxycarbonyloxy)ethyl, 1-(methoxycarbonyloxy)propyl, 1-(methoxycarbonyloxy)butyl, 1-(methoxycarbonyloxy)pentyl, 1-(methoxycarbonyloxy)hexyl, ethoxycarbonyloxymethyl, 1-(ethoxycarbonyloxy)ethyl, 1-(ethoxycarbonyloxy)propyl, 1-(ethoxycarbonyloxy)butyl, 1-(ethoxycarbonyloxy)pentyl, 1-(ethoxycarbonyloxy)hexyl, propoxycarbonyloxymethyl, 1-(propoxycarbonyloxy)ethyl, 1-(propoxycarbonyloxy)propyl, 1-(propoxycarbonyloxy)butyl, isopropoxycarbonyloxymethyl, 1-(isopropoxycarbonyloxy)ethyl, 1-(isopropoxycarbonyloxy)butyl, butoxycarbonyloxymethyl, 1-(butoxycarbonyloxy)ethyl, 1-(butoxycarbonyloxy)propyl, 1-(butoxycarbonyloxy)butyl, isobutoxycarbonyloxymethyl, 1-(isobutoxycarbonyloxy)ethyl, 1-(isobutoxycarbonyloxy)propyl, 1-(isobutoxycarbonyloxy)butyl, t-butoxycarbonyloxymethyl, 1-(t-butoxycarbonyloxy)ethyl, pentyloxycarbonyloxymethyl, 1-(pentyloxycarbonyloxy)ethyl, 1-(pentyloxycarbonyloxy)propyl, hexyloxycarbonyloxymethyl, 1-(hexyloxycarbonyloxy)ethyl or 1-(hexyloxycarbonyloxy)propyl; a $C_5$-$C_6$ cycloalkyloxycarbonyloxy $C_1$-$C_4$ alkyl group such as cyclopentyloxycarbonyloxymethyl, 1-(cyclopentyloxycarbonyloxy)ethyl, 1-(cyclopentyloxycarbonyloxy)propyl, 1-(cyclopentyloxycarbonyloxy)butyl, cyclohexyloxycarbonyloxymethyl, 1-(cyclohexyloxycarbonyloxy)ethyl, 1-(cyclohexyloxycarbonyloxy)propyl or 1-(cyclohexyloxycarbonyloxy)butyl; a [5-($C_1$-$C_4$ alkyl)-2-oxo-1,3-dioxolen-4-yl]methyl group such as (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl or (5-butyl-2-oxo-1,3-dioxolen-4-yl)methy; a [5-(phenyl, which may be optionally substituted with a $C_1$-$C_4$ alkyl, $C_1$-$C_4$ alkoxy or halogen atom(s))-2-oxo-1,3-dioxolen-4-yl]methyl group such as (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl or [5-(4-chlorophenyl)-2-oxo-1,3-dioxolen-4-yl]methyl; or a phthalidyl group, which may be optionally substituted with a $C_1$-$C_4$ alkyl or $C_1$-$C_4$ alkoxy group(s), such as phthalidyl, dimethylphthalidyl or dimethoxyphthalidyl, and is preferably a pivaloyloxymethyl group, phthalidyl group or (5-methyl-2-oxo-1,3-dioxolen-4-yl)methyl group, and more preferably a (5-methyl-2-oxo-1,3-dioxolen-4-yl)methyl group.

Any compound referred to herein is intended to represent such a specific compound as well as certain variations or forms. In particular, compounds referred to herein have asymmetric centres and therefore exist in different enantiomeric forms. All optical isomers and stereoisomers of the 1,2,4-trioxanes of formula (I) referred to herein, and mixtures thereof, are considered within the scope of the present invention. Thus any given compound referred to herein is intended to represent any one of a racemate, one or more enantiomeric forms, one or more diastereomeric forms, one or more atropisomeric forms, and mixtures thereof. Particularly, the 1,2,4-trioxanes of formula (I) may include enantiomers depending on their asymmetry or diastereoisomers. Stereoisomerism about the double bond is also possible, therefore in some cases the molecule could exist as an (E)-isomer or a (Z)-isomer. If the molecule contains several double bonds, each double bond will have its own stereoisomerism, that could be the same or different than the stereoisomerism of the other double bonds of the molecule. The single isomers and mixtures of isomers fall within the scope of the present invention.

Furthermore, compounds referred to herein may exist as geometric isomers (i.e., cis and trans isomers), as tautomers, or as atropisomers. Specifically, the term tautomer refers to one of two or more structural isomers of a compound, that exist in equilibrium and are readily converted from one isomeric form to another. Common tautomeric pairs are amine-imine, amide-imide, keto-enol, lactam-lactim, etc. Additionally, any compound referred to herein is intended to represent hydrates, solvates, and polymorphs, and mixtures thereof when such forms exist in the medium. In addition, compounds referred to herein may exist in isotopically-labelled forms. All geometric isomers, tautomers, atropisomers, hydrates, solvates, polymorphs, and isotopically labelled forms of the compounds referred to herein, and mixtures thereof, are considered within the scope of the present invention.

The trioxanes that are preferred as adjuvants to TKIs are exemplified by the structures shown in below in Figure 1. The compounds not bearing oxygen substituents on the spirocyclic pentene ring, exemplified by compounds T6 and T7, can be prepared according to published procedures ((C. W. Jefford, S. Kohmoto, D. Jaggi, G. Timári, J.-C. Rossier, M. Rudaz, O. Barbuzzi, D. Gérard, U. Burger, P. Kamalaprija, J. Mareda, G. Bernardinelli, I. Manzanares, C. J. Canfield, S. L. Fleck, B. L. Robinson, and W. Peters, *Helv. Chim. Acta* 1995, 78, 647-662) and methods further described (EP-A-1 286 316). Methods for the insertion of oxygen substituents into the cyclopentene moiety to provide, for example, trioxanes T53 and T59, have been described (EP-A-585 080). A typical procedure is the dye-sensitized photo-oxygenation of trioxane T45 to give trioxane T53. The latter on treatment with triethylamine and acetic anhydride affords trioxane T59.

Figure 1. Structures of preferred trioxanes

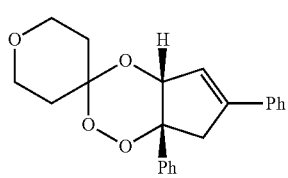

T41

$C_{22}H_{22}O_4$

Mol. Wt 350.42

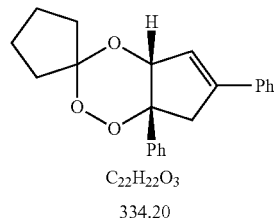

T6

$C_{22}H_{22}O_3$ 334.20

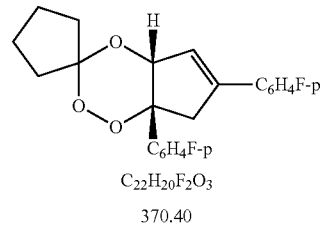

T7

$C_{22}H_{20}F_2O_3$ 370.40

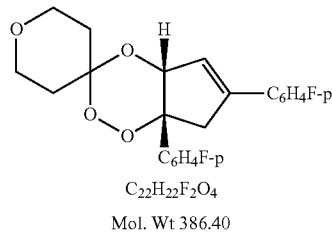

T45

$C_{22}H_{22}F_2O_4$

Mol. Wt 386.40

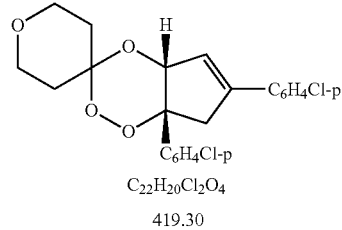

T46

$C_{22}H_{20}Cl_2O_4$ 419.30

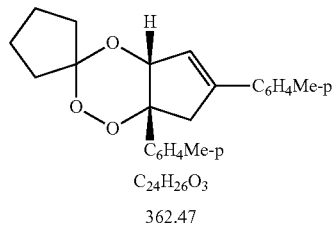

T11

$C_{24}H_{26}O_3$ 362.47

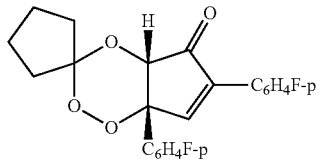

T14

$C_{22}H_{18}F_2O_4$

Mol. Wt 384.37

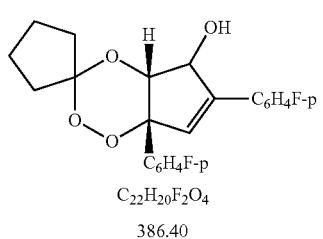

T16

$C_{22}H_{20}F_2O_4$ 386.40

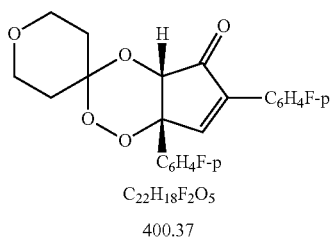

T59

$C_{22}H_{18}F_2O_5$ 400.37

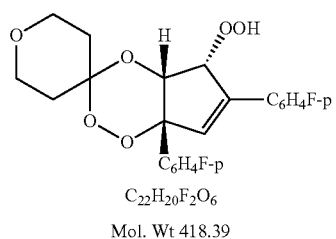

T53

$C_{22}H_{20}F_2O_6$

Mol. Wt 418.39

Preferred 1,2,4-trioxanes of formula (I) or a pharmaceutically acceptable salt, ester, solvate, tautomer or stereoisomer thereof for use as an adjuvant for a tyrosine kinase inhibitor to enhance the activity of said tyrosine kinase inhibitor in a method for the treatment of a patient suffering from cancer in accordance with the first aspect of the present invention include:

- a 1,2,4-trioxane of formula (I) or a pharmaceutically acceptable salt, ester, solvate, tautomer or stereoisomer thereof for use as an adjuvant according to the first aspect of the present invention, wherein said 1,2,4-trioxane of formula (I) or a pharmaceutically acceptable salt, ester, solvate, tautomer or stereoisomer thereof and said TKI are either administered simultaneously or stepwise.
- a 1,2,4-trioxane of formula (I) or a pharmaceutically acceptable salt, ester, solvate, tautomer or stereoisomer thereof for use as an adjuvant according to the first aspect of the present invention, wherein each of substituents $R^1$ and $R^2$, which can be the same or different, represents a linear or branched alkyl group having from 1 to 6 carbon atoms, a linear or branched alkenyl group having from 2 to 6 carbon atoms or a linear or branched alkynyl group having from 2 to 6 carbon atoms, each of which can optionally be substituted with one or more substituents chosen from substituents $R^x$, or $R^1$ and $R^2$ taken together with the carbon atom to which they are attached can form an alicyclic group having from 4 to 6 carbon atoms which may optionally be interrupted by one or more oxygen, sulphur or nitrogen atoms, wherein said alicyclic group may optionally be substituted with one or more substituents chosen from substituents $R^x$.
- a 1,2,4-trioxane of formula (I) or a pharmaceutically acceptable salt, ester, solvate, tautomer or stereoisomer thereof for use as an adjuvant according to the first aspect of the present invention, wherein each of substituents $R^1$ and $R^2$, which can be the same or different, represents a methyl, ethyl, isopropyl, t-butyl, vinyl or ethynyl group which can optionally be substituted with one or more substituents chosen from $R^{x'}$, or $R^1$ and $R^2$ taken together with the carbon atom to which they are attached can form an alicyclic group having 5 or 6 carbon atoms which may optionally be interrupted by one or more oxygen atoms, wherein said alicyclic group may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms.
- a 1,2,4-trioxane of formula (I) or a pharmaceutically acceptable salt, ester, solvate, tautomer or stereoisomer thereof for use as an adjuvant according to the first aspect of the present invention, wherein $Ar^1$ and $Ar^2$, which can be the same or different, represents an aromatic group selected from aryl groups having from 6 to 12 carbon atoms in one or more rings, and 5- to 8-membered heteroaryl groups having one or more rings, wherein said aryl group or said heteroaryl group may optionally be substituted with one or more substituents chosen from substituents $R^x$.
- a 1,2,4-trioxane of formula (I) or a pharmaceutically acceptable salt, ester, solvate, tautomer or stereoisomer thereof for use as an adjuvant according to the first aspect of the present invention, wherein $Ar^1$ and $Ar^2$, which can be the same or different, represents a group selected from a phenyl group, a pyridine group, a pyrimidinyl group, a furyl group, a pyrrolyl group and a thienyl group, wherein said groups may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms.
- a 1,2,4-trioxane of formula (I) or a pharmaceutically acceptable salt, ester, solvate, tautomer or stereoisomer thereof for use as an adjuvant according to the first aspect of the present invention, wherein each of the substituents X and Y, which can be the same or different, represents a group selected from a hydrogen atom or a functional group that contains oxygen, sulphur or nitrogen selected from an oxo group, a hydroxyl group, a hydroperoxy group, an alkoxy group having from 1 to 6 carbon atoms, a group of formula $OCOR^y$ wherein $R^y$ is an alkyl group having from 1 to 6 carbon atoms, a group of formula $OCOOR^y$ wherein $R^y$ is an alkyl group having from 1 to 6 carbon atoms, a group of formula $=NR^y$ wherein $R^y$ is a hydrogen atom or an alkyl group having from 1 to 6 carbon atoms, a group of formula $NR^yR^z$ wherein each of $R^y$ and $R^z$, which can be the same or different, can be a hydrogen atom or an alkyl group having from 1 to 6 carbon atoms, a group of formula $NR^yCOR^z$, wherein each of $R^y$ and $R^z$ can the same or different and is hydrogen or an alkyl group having from 1 to 6 carbon atoms, a nitro group, a thione group, a thiol group, a disulfane group, a group of formula $S(O)R^y$ wherein $R^y$ is a hydrogen atom or an alkyl group having from 1 to 6 carbon atoms and a group of formula $SO_2R$ wherein $R^y$ is a hydrogen atom or an alkyl group having from 1 to 6 carbon atoms.

a 1,2,4-trioxane of formula (I) or a pharmaceutically acceptable salt, ester, solvate, tautomer or stereoisomer thereof for use as an adjuvant according to the first aspect of the present invention, wherein each of the substituents X and Y, which can be the same or different, represents a substituent selected from hydrogen atom, an oxo group, a hydroxyl group, a hydroperoxy group, a group of formula $OCOOR^y$ wherein $R^y$ is an alkyl group having from 1 to 6 carbon atoms, an amino group, an imine group, a thione group and a thiol group, and is preferably selected from a hydrogen atom, an oxo group, a hydroxyl group and a hydroperoxy group.

a 1,2,4-trioxane of formula (I) for use as an adjuvant according to the first aspect of the present invention, selected from the following group:

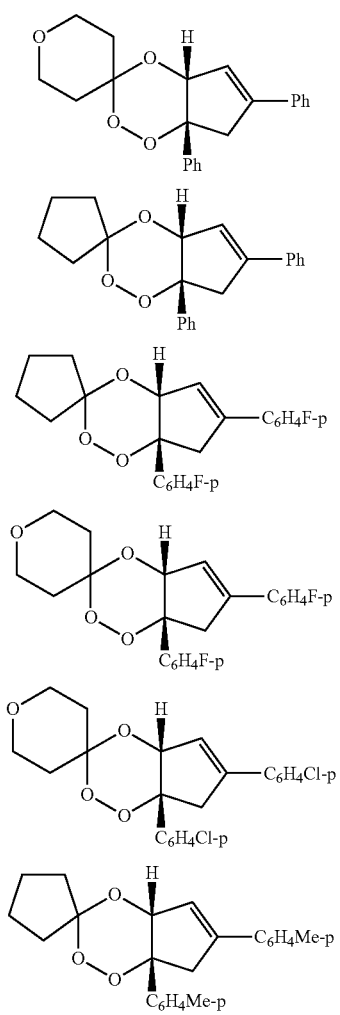

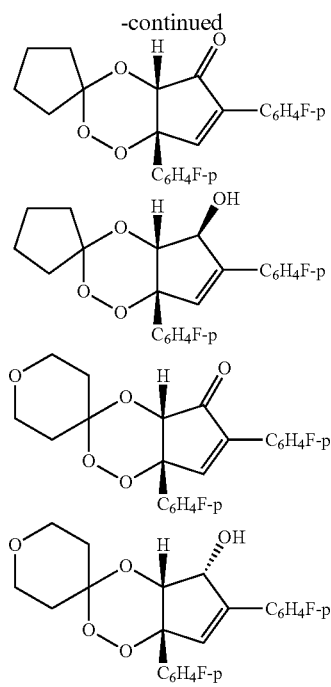

or a pharmaceutically acceptable salt, ester, solvate, tautomer or stereoisomer thereof a 1,2,4-trioxane of formula (I) or a pharmaceutically acceptable salt, ester, solvate, tautomer or stereoisomer thereof for use as an adjuvant according to the first aspect of the present invention, wherein the tyrosine kinase inhibitor is an inhibitor of a kinase selected from an epidermal growth factor receptor (EGFR), a platelet derived growth factor (PDGF), bcr-abl, c-KIT kinase, FLT kinase, a platelet derived growth factor (PDGFR), a vascular endothelial growth factor (VEGFR) and Src-family non-receptor kinases.

a 1,2,4-trioxane of formula (I) or a pharmaceutically acceptable salt, ester, solvate, tautomer or stereoisomer thereof for use as an adjuvant according to the first aspect of the present invention, wherein the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol, and preferably imatinib, gefitinib, erlotinib, lapatinib, canertinib, vatalanib, sorafenib and genistein.

a 1,2,4-trioxane of formula (I) or a pharmaceutically acceptable salt, ester, solvate, tautomer or stereoisomer thereof for use as an adjuvant according to the first aspect of the present invention, wherein:
each of substituents $R^1$ and $R^2$, which can be the same or different, represents a linear or branched alkyl group having from 1 to 6 carbon atoms, a linear or branched alkenyl group having from 2 to 6 carbon atoms or a linear or branched alkynyl group having from 2 to 6 carbon atoms, each of which can optionally be substituted with one or more substituents chosen from substituents $R^x$, or $R^1$ and $R^2$ taken together with the carbon atom to which they are attached can form an alicyclic group having from 4 to 6 carbon atoms which may optionally be interrupted by one or more oxygen, sulphur or nitrogen atoms, wherein said alicyclic group may optionally be substituted with one or more substituents chosen from substituents $R^x$;

$Ar^1$ and $Ar^2$, which can be the same or different, represents an aromatic group selected from aryl groups having from 6 to 12 carbon atoms in one or more rings, and 5- to 8-membered heteroaryl groups having one or more rings, wherein said aryl group or said heteroaryl group may optionally be substituted with one or more substituents chosen from substituents $R^x$;

each of the substituents X and Y, which can be the same or different, represents a substituent selected from a hydrogen atom or a functional group that contains oxygen, sulphur or nitrogen selected from an oxo group, a hydroxyl group, a hydroperoxy group, an alkoxy group having from 1 to 6 carbon atoms, a group of formula $OCOR^y$ wherein $R^y$ is an alkyl group having from 1 to 6 carbon atoms, a group of formula $OCOOR^y$ wherein $R^y$ is an alkyl group having from 1 to 6 carbon atoms, a group of formula $=NR^y$ wherein $R^y$ is a hydrogen atom or an alkyl group having from 1 to 6 carbon atoms, a group of formula $NR^yR^z$ wherein each of $R^y$ and $R^z$, which can be the same or different, can be a hydrogen atom or an alkyl group having from 1 to 6 carbon atoms, a group of formula $NR^yCOR^z$, wherein each of $R^y$ and $R^z$ can the same or different and is hydrogen or an alkyl group having from 1 to 6 carbon atoms, a nitro group, a thione group, a thiol group, a disulfane group, a group of formula $S(O)R^y$ wherein $R^y$ is a hydrogen atom or an alkyl group having from 1 to 6 carbon atoms and a group of formula $SO_2R$ wherein $R^y$ is a hydrogen atom or an alkyl group having from 1 to 6 carbon atoms;

the substituent Z represents an epoxide oxygen atom attached to the 5,6 or 6,7 positions or a pair of electrons forming a double bond at the 5,6 or 6,7 positions; and the tyrosine kinase inhibitor is an inhibitor of a kinase selected from an epidermal growth factor receptor (EGFR), platelet derived growth factor (PDGF), bcr-abl, c-KIT kinase, FLT kinase, platelet derived growth factor (PDGFR), vascular endothelial growth factor (VEGFR) and Src-family non-receptor kinases.

a 1,2,4-trioxane of formula (I) or a pharmaceutically acceptable salt, ester, solvate, tautomer or stereoisomer thereof for use as an adjuvant according to the first aspect of the present invention, wherein:

$R^1$ and $R^2$, which can be the same or different, represents a methyl, ethyl, isopropyl, t-butyl, vinyl or ethynyl group which can optionally be substituted with one or more substituents chosen from $R^{x'}$, or $R^1$ and $R^2$ taken together with the carbon atom to which they are attached can form an alicyclic group having 5 or 6 carbon atoms which may optionally be interrupted by one or more oxygen atoms, wherein said alicyclic group may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms;

$Ar^1$ and $Ar^2$, which can be the same or different, represents a substituent selected from a phenyl group, a pyridine group, a pyrimidinyl group, a furyl group, a pyrrolyl group and a thienyl group, wherein said groups may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y''}R^{z''}$ wherein each of $R^{y''}$ and $R^{z''}$ is the same or different and is hydrogen or an alkyl group having from 1 to 6 carbon atoms, cyano groups, nitro groups, hydroxyl groups, groups of formula $OCOOR^{y'''}$ and groups of formula $OCOR^{y'''}$ wherein $R^{y'''}$ is an alkyl group having from 1 to 6 carbon atoms;

each of the substituents X and Y, which can be the same or different, represents a substituent selected from hydrogen atom, an oxo group, a hydroxyl group, a hydroperoxy group, a group of formula $OCOR^y$ wherein $R^y$ is an alkyl group having from 1 to 6 carbon atoms, an amino group, an imine group, a thione group and a thiol group, and is preferably selected from a hydrogen atom, an oxo group, a hydroxyl group and a hydroperoxy group;

the substituent Z represents a pair of electrons forming a double bond at the 5,6 or 6,7 positions; and the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol, and preferably imatinib, gefitinib, erlotinib, lapatinib, canertinib, vatalanib, sorafenib and genistein.

a 1,2,4-trioxane of formula (I) for use as an adjuvant according to the first aspect of the present invention, wherein:

the 1,2,4-trioxane of formula (I) is selected from the following compounds or a pharmaceutically acceptable salt, ester, solvate, tautomer or stereoisomer thereof

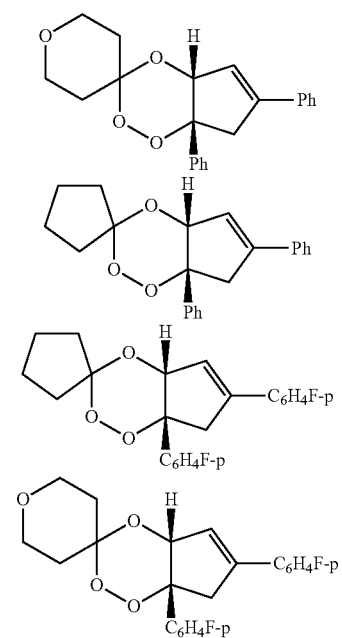

-continued

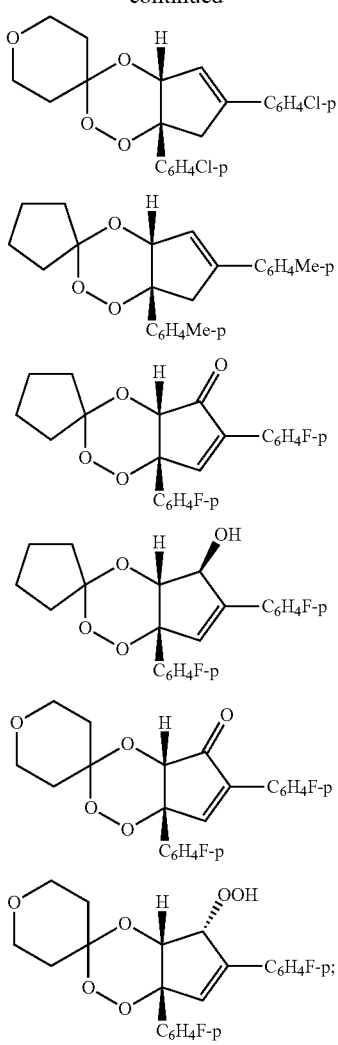

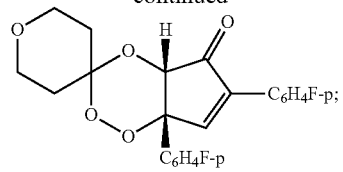

and
the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol, and preferably imatinib, gefitinib, erlotinib, lapatinib, canertinib, vatalanib, sorafenib and genistein.

a 1,2,4-trioxane of formula (I) for use as an adjuvant according to the first aspect of the present invention, wherein the 1,2,4-trioxane of formula (I) is selected from the following compounds or a pharmaceutically acceptable salt, ester, solvate, tautomer or stereoisomer thereof:

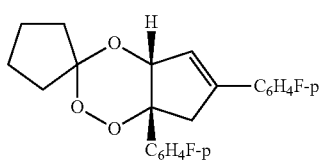

and
the tyrosine kinase inhibitor is selected from imatinib and genistein.

a 1,2,4-trioxane of formula (I) or a pharmaceutically acceptable salt, ester, solvate, tautomer or stereoisomer thereof for use as an adjuvant according to the first aspect of the present invention, wherein the molar ratio of tyrosine kinase inhibitor to the 1,2,4-trioxane of formula (I) or a pharmaceutically acceptable salt, ester, solvate, tautomer or stereoisomer thereof adjuvant is from 50:1 to 1:1, preferably 20:1 to 1:1 and most preferably 15:1 to 5:1.

Preferred pharmaceutical compositions comprising a tyrosine kinase inhibitor as an active ingredient and a 1,2,4-trioxane of formula (I) adjuvant or a pharmaceutically acceptable salt, ester, solvate, tautomer or stereoisomer thereof in an amount sufficient to enhance the activity of the tyrosine kinase inhibitor, and a pharmaceutically acceptable carrier in accordance with the second aspect of the present invention include:

a pharmaceutical composition according to the second aspect of the present invention, wherein said pharmaceutical composition is formulated such that said 1,2,4-trioxane of formula (I) or a pharmaceutically acceptable salt, ester, solvate, tautomer or stereoisomer thereof and said TKI can be either administered simultaneously or stepwise.

a pharmaceutical composition according to the second aspect of the present invention, wherein each of substituents $R^1$ and $R^2$, which can be the same or different, represents a linear or branched alkyl group having from 1 to 6 carbon atoms, a linear or branched alkenyl group having from 2 to 6 carbon atoms or a linear or branched alkynyl group having from 2 to 6 carbon atoms, each of which can optionally be substituted with one or more substituents chosen from substituents $R^x$, or $R^1$ and $R^2$ taken together with the carbon atom to which they are attached can form an alicyclic group having from 4 to 6 carbon atoms which may optionally be interrupted by one or more oxygen, sulphur or nitrogen atoms, wherein said alicyclic group may optionally be substituted with one or more substituents chosen from substituents $R^x$.

a pharmaceutical composition according to the second aspect of the present invention, wherein each of substituents $R^1$ and $R^2$, which can be the same or different, represents a methyl, ethyl, isopropyl, t-butyl, vinyl or ethynyl group which can optionally be substituted with one or more substituents chosen from $R^{x'}$, or $R^1$ and $R^2$ taken together with the carbon atom to which they are attached can form an alicyclic group having 5 or 6 carbon atoms which may optionally be interrupted by one or more oxygen atoms, wherein said alicyclic group may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms.

a pharmaceutical composition according to the second aspect of the present invention, wherein $Ar^1$ and $Ar^2$, which can be the same or different, represents an aromatic group selected from aryl groups having from 6 to 12 carbon atoms in one or more rings, and 5- to 8-membered heteroaryl groups having one or more rings, wherein said aryl group or said heteroaryl group may optionally be substituted with one or more substituents chosen from substituents $R^x$.

a pharmaceutical composition according to the second aspect of the present invention, wherein $Ar^1$ and $Ar^2$, which can be the same or different, represents a group selected from a phenyl group, a pyridine group, a pyrimidinyl group, a furyl group, a pyrrolyl group and a thienyl group, wherein said groups may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y'''}$ and groups of formula $OCOR^{y'''}$ wherein $R^{y'''}$ is an alkyl group having from 1 to 6 carbon atoms.

a pharmaceutical composition according to the second aspect of the present invention, wherein each of the substituents X and Y, which can be the same or different, represents a group selected from a hydrogen atom or a functional group that contains oxygen, sulphur or nitrogen selected from an oxo group, a hydroxyl group, a hydroperoxy group, an alkoxy group having from 1 to 6 carbon atoms, a group of formula $OCOR^y$ wherein $R^y$ is an alkyl group having from 1 to 6 carbon atoms, a group of formula $OCOOR^y$ wherein $R^y$ is an alkyl group having from 1 to 6 carbon atoms, a group of formula $=NR^y$ wherein $R^y$ is a hydrogen atom or an alkyl group having from 1 to 6 carbon atoms, a group of formula $NR^yR^z$ wherein each of $R^y$ and $R^z$, which can be the same or different, can be a hydrogen atom or an alkyl group having from 1 to 6 carbon atoms, a group of formula $NR^yCOR^z$, wherein each of $R^y$ and $R^z$ can the same or different and is hydrogen or an alkyl group having from 1 to 6 carbon atoms, a nitro group, a thione group, a thiol group, a disulfane group, a group of formula $S(O)R^y$ wherein $R^y$ is a hydrogen atom or an alkyl group having from 1 to 6 carbon atoms and a group of formula $SO_2R$ wherein $R^y$ is a hydrogen atom or an alkyl group having from 1 to 6 carbon atoms.

a pharmaceutical composition according to the second aspect of the present invention, wherein each of the substituents X and Y, which can be the same or different, represents a substituent selected from hydrogen atom, an oxo group, a hydroxyl group, a hydroperoxy group, a group of formula $OCOOR^y$ wherein $R^y$ is an alkyl group having from 1 to 6 carbon atoms, an amino group, an imine group, a thione group and a thiol group, and is preferably selected from a hydrogen atom, an oxo group, a hydroxyl group and a hydroperoxy group.

a pharmaceutical composition according to the second aspect of the present invention, wherein the 1,2,4-trioxane of formula (I) is selected from the following group:

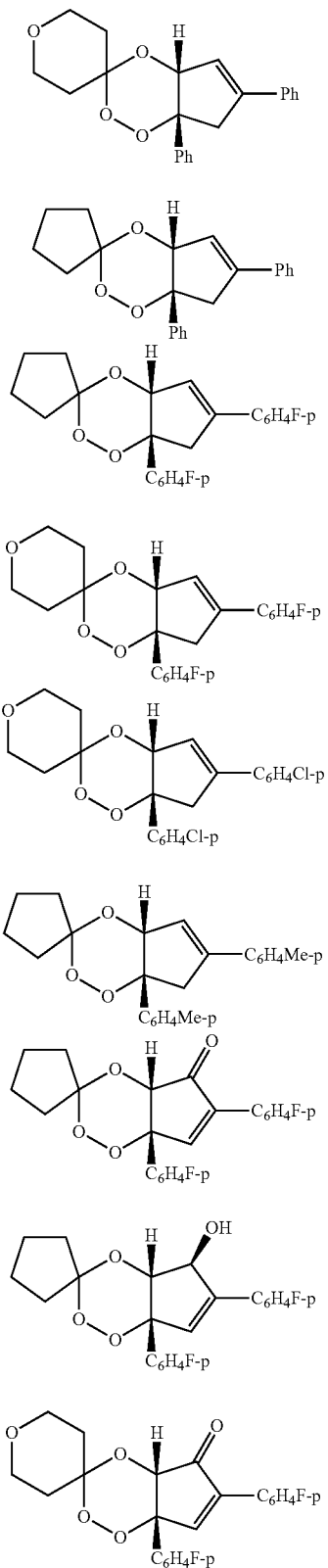

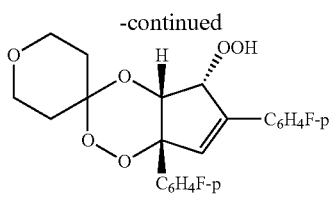

or a pharmaceutically acceptable salt, ester, solvate, tautomer or stereoisomer thereof.

a pharmaceutical composition according to the second aspect of the present invention, wherein the tyrosine kinase inhibitor is an inhibitor of a kinase selected from an epidermal growth factor receptor (EGFR), a platelet derived growth factor (PDGF), bcr-abl, c-KIT kinase, FLT kinase, a platelet derived growth factor (PDGFR), vascular endothelial growth factor (VEGFR) and Src-family non-receptor kinases.

a pharmaceutical composition according to the second aspect of the present invention, wherein the tyrosine kinase inhibitor is selected from imatinib, gefitinib, erlotinib, lapatinib, canertinib, vatalanib, sorafenib, axitinib, dasatinib, pazopanib, sunitinib, semaxinib, bosutinib, cabozatinib, crizotinib, masitinib, neratinib B, regorafenib, vandetanib, genistein, emodin and radiciol, and preferably imatinib, gefitinib, erlotinib, lapatinib, canertinib, vatalanib, sorafenib and genistein.

a pharmaceutical composition according to according to the second aspect of the present invention, wherein the 1,2,4-trioxane of formula (I) adjuvant or a pharmaceutically acceptable salt, ester, solvate, tautomer or stereoisomer thereof is as defined below:
each of substituents $R^1$ and $R^2$, which can be the same or different, represents a linear or branched alkyl group having from 1 to 6 carbon atoms, a linear or branched alkenyl group having from 2 to 6 carbon atoms or a linear or branched alkynyl group having from 2 to 6 carbon atoms, each of which can optionally be substituted with one or more substituents chosen from substituents $R^x$, or $R^1$ and $R^2$ taken together with the carbon atom to which they are attached can form an alicyclic group having from 4 to 6 carbon atoms which may optionally be interrupted by one or more oxygen, sulphur or nitrogen atoms, wherein said alicyclic group may optionally be substituted with one or more substituents chosen from substituents $R^x$;
$Ar^1$ and $Ar^2$, which can be the same or different, represents an aromatic group selected from aryl groups having from 6 to 12 carbon atoms in one or more rings, and 5- to 8-membered heteroaryl groups having one or more rings, wherein said aryl group or said heteroaryl group may optionally be substituted with one or more substituents chosen from substituents $R^x$;
each of the substituents X and Y, which can be the same or different, represents a substituent selected from a hydrogen atom or a functional group that contains oxygen, sulphur or nitrogen selected from an oxo group, a hydroxyl group, a hydroperoxy group, an alkoxy group having from 1 to 6 carbon atoms, a group of formula $OCOR^y$ wherein $R^y$ is an alkyl group having from 1 to 6 carbon atoms, a group of formula $OCOOR^y$ wherein $R^y$ is an alkyl group having from 1 to 6 carbon atoms, a group of formula $=NR^y$ wherein $R^y$ is a hydrogen atom or an alkyl group having from 1 to 6 carbon atoms, a group of formula $NR^yR^z$ wherein each of $R^y$ and $R^z$, which can be the same or different, can be a hydrogen atom or an alkyl group having from 1 to 6 carbon atoms, a group of formula $NR^yCOR^z$, wherein each of $R^y$ and $R^z$ can the same or different and is hydrogen or an alkyl group having from 1 to 6 carbon atoms, a nitro group, a thione group, a thiol group, a disulfane group, a group of formula $S(O)R^y$ wherein $R^y$ is a hydrogen atom or an alkyl group having from 1 to 6 carbon atoms and a group of formula $SO_2R$ wherein $R^y$ is a hydrogen atom or an alkyl group having from 1 to 6 carbon atoms; and
the substituent Z represents an epoxide oxygen atom attached to the 5,6 or 6,7 positions or a pair of electrons forming a double bond at the 5,6 or 6,7 positions; and
the tyrosine kinase inhibitor is an inhibitor of a kinase selected from an epidermal growth factor receptor (EGFR), platelet derived growth factor (PDGF), bcr-abl, c-KIT kinase, FLT kinase, platelet derived growth factor (PDGFR), vascular endothelial growth factor (VEGFR) and Src-family non-receptor kinases.

a pharmaceutical composition according to according to the second aspect of the present invention, wherein the 1,2,4-trioxane of formula (I) adjuvant or a pharmaceutically acceptable salt, ester, solvate, tautomer or stereoisomer thereof is as defined below:
$R^1$ and $R^2$, which can be the same or different, represents a methyl, ethyl, isopropyl, t-butyl, vinyl or ethynyl group which can optionally be substituted with one or more substituents chosen from $R^{x'}$, or $R^1$ and $R^2$ taken together with the carbon atom to which they are attached can form an alicyclic group having 5 or 6 carbon atoms which may optionally be interrupted by one or more oxygen atoms, wherein said alicyclic group may optionally be substituted with one or more substituents chosen from substituents $R^{x'}$,
wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms;
$Ar^1$ and $Ar^2$, which can be the same or different, represents a substituent selected from a phenyl group, a pyridine group, a pyrimidinyl group, a furyl group, a pyrrolyl group and a thienyl group, wherein said groups may optionally be substituted with one or more substituents chosen from substituents $R^{x'}$,
wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms;
each of the substituents X and Y, which can be the same or different, represents a substituent selected from hydrogen atom, an oxo group, a hydroxyl group, a hydroperoxy group, a group of formula $OCOR^y$ wherein $R^y$ is an alkyl group having from 1 to 6 carbon atoms, an amino group, an imine group, a thione group and a thiol group, and is preferably selected from a hydrogen atom, an oxo group, a hydroxyl group and a hydroperoxy group; and the substituent Z represents a pair of electrons forming a double bond at the 5,6 or 6,7 positions; and the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol, and preferably imatinib, gefitinib, erlotinib, lapatinib, canertinib, vatalanib, sorafenib and genistein.

a pharmaceutical composition according to according to the second aspect of the present invention, wherein:

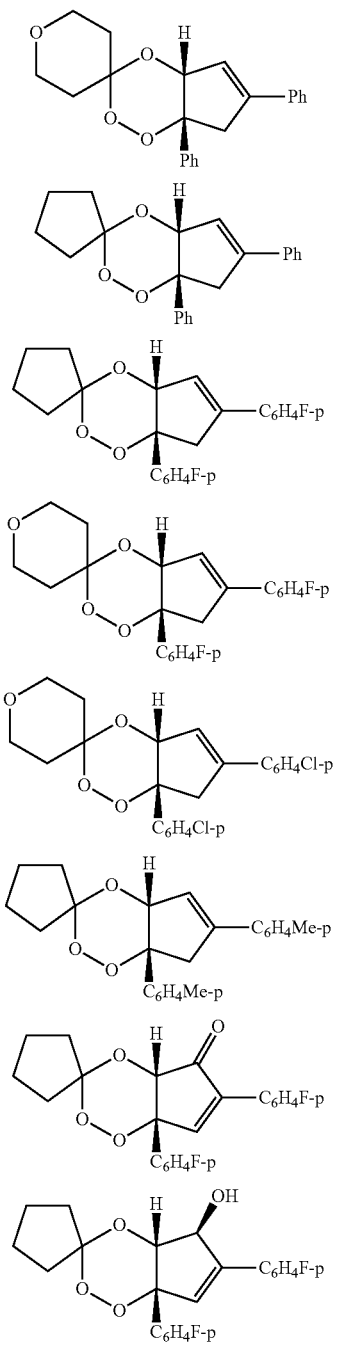

-continued

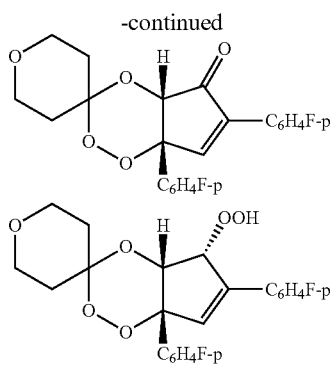

the 1,2,4-trioxane of formula (I) adjuvant is selected from the following compounds or a pharmaceutically acceptable salt, ester, solvate, tautomer or stereoisomer thereof; and the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol, and preferably imatinib, gefitinib, erlotinib, lapatinib, canertinib, vatalanib, sorafenib and genistein.

a pharmaceutical composition according to according to the second aspect of the present invention, wherein the 1,2,4-trioxane of formula (I) is selected from the following compounds or a pharmaceutically acceptable salt, ester, solvate, tautomer or stereoisomer thereof:

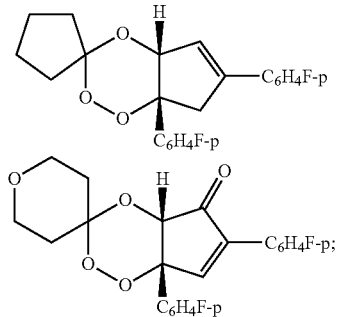

and the tyrosine kinase inhibitor is selected from imatinib and genistein.

a pharmaceutical composition according to the second aspect of the present invention, wherein the molar ratio of tyrosine kinase inhibitor active ingredient to the 1,2,4-trioxane adjuvant of formula (I) or a pharmaceutically acceptable salt, ester, solvate, tautomer or stereoisomer thereof is from 50:1 to 1:1, preferably 20:1 to 1:1 and most preferably 15:1 to 5:1.

Examples of the administration form of a pharmaceutical composition according to the second aspect of the present invention include without limitation oral, topical, parenteral, sublingual, rectal, vaginal, ocular, and intranasal. Parenteral administration includes subcutaneous injections, intravenous, intramuscular, intrasternal injection or infusion techniques. Preferably, the compositions are administered parenterally or orally. Pharmaceutical compositions of the invention can be formulated so as to allow the tyrosine kinase active ingredient and the 1,2,4-trioxane of formula (I) or a pharmaceutically acceptable salt, ester, solvate, tautomer or stereoisomer thereof of the present invention to be bioavailable upon administration of the composition to an animal, preferably human. Compositions can take the form of one or more dosage units, where for example, a tablet can be a single dosage unit, and a container comprising tyrosine kinase active of the present invention and a pharmaceutically acceptable salt, ester, solvate, tautomer or stereoisomer thereof in aerosol form can hold a plurality of dosage units.

Alternatively, rather than formulating the compositions so that the tyrosine kinase inhibitor as the active ingredient and the 1,2,4-trioxane adjuvant of formula (I) or a pharmaceutically acceptable salt, ester, solvate, tautomer or stereoisomer are delivered simultaneously in a single dosage form, they can be formulated so that the 1,2,4-trioxane adjuvant of formula (I) or a pharmaceutically acceptable salt, ester, solvate, tautomer or stereoisomer thereof can be administered separately either before or after the administration of the tyrosine kinase inhibitor active ingredient, i.e. step-wise administration.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, for example, inhalatory administration. The term "carrier" refers to a diluent or excipient, with which the tyrosine kinase inhibitor as the active ingredient and the 1,2,4-trioxane adjuvant of formula (I) or a pharmaceutically acceptable salt, ester, solvate, tautomer or stereoisomer of the present invention is administered. Such pharmaceutical carriers can be liquids, such as water and oils, including those of petroleum, animal, vegetable or synthetic origin, such as corn oil, lipomul, olive oil, peanut oil, soybean oil, mineral oil, sesame oil and the like, preferably corn oil, lipomul and olive oil. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the tyrosine kinase inhibitor as the active ingredient and the 1,2,4-trioxane adjuvant of formula (I) or a pharmaceutically acceptable salt, ester, solvate, tautomer or stereoisomer of the present invention of the present invention or compositions and pharmaceutically acceptable carriers are sterile. Water is a preferred carrier when the tyrosine kinase inhibitor as the active ingredient and the 1,2,4-trioxane adjuvant of formula (I) or a pharmaceutically acceptable salt, ester, solvate, tautomer or stereoisomer of the present invention are administered intravenously. Saline solutions and aqueous dextrose and glycerol solutions can also be employed as liquid carriers, particularly for injectable solutions.

Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When the composition is in the form of a capsule (e.g. a gelatin capsule), it can contain, in addition to materials of the above type, a liquid carrier such as polyethylene glycol, cyclodextrin or a fatty oil.

The composition can be in the form of a liquid, e.g. an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

One preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, the tyrosine kinase inhibitor as the active ingredient and the 1,2,4-trioxane adjuvant of formula (I) or a pharmaceutically acceptable salt, ester, solvate, tautomer or stereoisomer of the present invention of the present invention are administered intravenously.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant.

The amount of the tyrosine kinase inhibitor as the active ingredient and the 1,2,4-trioxane adjuvant of formula (I) or a pharmaceutically acceptable salt, ester, solvate, tautomer or stereoisomer of the present invention that is effective in the treatment of a particular disorder or condition will depend on the nature of the disorder or condition, and can be determined by standard clinical techniques. In addition, in vitro or in vivo assays can optionally be employed to help identify optimal dosage ranges and, in particular ratios of tyrosine kinase inhibitor to 1,2,4-trioxane adjuvant of formula (I) or a pharmaceutically acceptable salt, ester, solvate, tautomer or stereoisomer. The precise dose to be employed in the compositions will also depend on the route of administration, and the seriousness of the disease or disorder, and should be decided according to the judgment of the practitioner and each patient's circumstances.

The compositions comprise an effective amount of a 1,2,4-trioxane adjuvant of formula (I) or a pharmaceutically acceptable salt, ester, solvate, tautomer or stereoisomer of the present invention and a tyrosine kinase inhibitor as active ingredient such that a suitable dosage will be obtained. The correct dosage of the compounds will vary according to the particular formulation, the mode of application, and its particular site, host and the disease being treated, e.g. cancer and, if so, what type of tumor. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

In the treatment of cancer, the molar ratio of tyrosine kinase inhibitor active ingredient to the 1,2,4-trioxane adjuvant of formula (I) or a pharmaceutically acceptable salt, ester, solvate, tautomer or stereoisomer thereof may be from 50:1 to 1:1, preferably from 20:1 to 1:1 and most preferably from 15:1 to 5:1, e.g. 10:1.

Typically, the amount of tyrosine kinase inhibitor active ingredient and 1,2,4-trioxane adjuvant of formula (I) or a pharmaceutically acceptable salt, ester, solvate, tautomer or stereoisomer thereof is at least about 0.01% by weight of the composition, preferably in the ratios of TKI active ingredient to 1,2,4-trioxane adjuvant set out above. When intended for oral administration, this amount can be varied to range from about 0.1% to about 80% by weight of the composition. Preferred oral compositions can comprise from about 4% to about 50% of the tyrosine kinase inhibitor active ingredient of the present invention and 1,2,4-trioxane adjuvant of formula (I) or a pharmaceutically acceptable salt, ester, solvate, tautomer or stereoisomer thereof by weight of the composition, preferably in the ratios of TKI active ingredient to 1,2,4-trioxane adjuvant set out above.

Preferred compositions of the present invention are prepared so that a parenteral dosage unit contains from about 0.01% to about 2% by weight of the tyrosine kinase inhibitor active ingredient and 1,2,4-trioxane adjuvant of formula (I) or a pharmaceutically acceptable salt, ester, solvate, tautomer or stereoisomer thereof of the present invention, preferably in the ratios of TKI active ingredient to 1,2,4-trioxane adjuvant set out above.

For intravenous administration, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight of tyrosine kinase inhibitor active ingredient and 1,2,4-trioxane adjuvant of formula (I) or a pharmaceutically acceptable salt, ester, solvate, tautomer or stereoisomer thereof, preferably in the ratios of TKI active ingredient to 1,2,4-trioxane adjuvant set out above.

The compositions can be administered by any convenient route, for example by infusion or bolus injection, by absorption through epithelial or mucocutaneous linings.

In specific embodiments, it can be desirable to administer the compositions locally to the area in need of treatment. In one embodiment, administration can be by direct injection at the site (or former site) of a cancer, tumor or neoplastic or pre-neoplastic tissue.

Pulmonary administration can also be employed, e.g. by use of an inhaler or nebulizer, and formulation with an aerosolizing agent, or via perfusion in a fluorocarbon or synthetic pulmonary surfactant. In certain embodiments, the compositions can be formulated as a suppository, with traditional binders and carriers such as triglycerides.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

The pharmaceutical compositions can be prepared using methodology well known in the pharmaceutical art. For example, a composition intended to be administered by injection can be prepared by combining a tyrosine kinase inhibitor active ingredient and 1,2,4-trioxane adjuvant of formula (I) or a pharmaceutically acceptable salt, ester, solvate, tautomer or stereoisomer thereof of the present invention with water so as to form a solution. A surfactant can be added to facilitate the formation of a homogeneous solution or suspension.

As noted in the third aspect of the present invention, it has been found that the compositions of the present invention are particularly effective in the treatment of cancer.

Thus, as described earlier, the third aspect of the present invention provides a pharmaceutical composition as defined above for use in a method for the treatment of cancer, for use in a method for the treatment of cancer selected from lymphomas (e.g. Hodgkin's disease and non-Hodgkin's Lymphoma), breast cancer, colorectal cancer, endometrial cancer, kidney cancer, gastrointestinal tumors, nonsmall cell lung cancer, melanoma, leukaemias, lung cancer renal carcinoma, solid tumors such as sarcoma and carcinomas, melanoma, mesothelioma, multiple myeloma, pancreatic cancer, osteosarcoma, ovarian cancer, prostate cancer and renal cancer).

In a preferred embodiment the cancer is lymphoma, breast cancer, leukemia, gastrointestinal tumors, nonsmall cell lung cancer, melanoma, renal carcinoma, multiple myeloma, kidney cancer, colon cancer, pancreatic cancer, lung cancer, ovarian cancer and prostate cancer, particularly lymphoma and breast cancer.

The fifth aspect of the present invention provides a method for the treatment of cancer comprising administering to a patient in need thereof a tyrosine kinase inhibitor as defined above as an active ingredient and a 1,2,4-trioxane of formula (I) adjuvant or a pharmaceutically acceptable salt, ester, solvate, tautomer or stereoisomer thereof as defined above in an amount sufficient to enhance the activity of the tyrosine kinase inhibitor.

The sixth aspect of the present invention provides use of a 1,2,4-trioxane of formula (I) adjuvant or a pharmaceutically acceptable salt, ester, solvate, tautomer or stereoisomer thereof as defined above in the manufacture of a medicament further comprising a tyrosine kinase inhibitor as defined above as an active ingredient for the treatment of cancer.

The compositions of the present invention are useful for inhibiting the multiplication of a tumor cell or cancer cell, or for treating cancer in an animal. The compositions of the present invention can be used accordingly in a variety of settings for the treatment of animal cancers.

As discussed above, the increase in activity achieved through use of the use of the 1,2,4-trioxanes of formula (I) as adjuvants for the tyrosine kinase inhibitors means that a much reduced dosage of the active ingredient is required to be effective, thus reducing toxicity and associated side-effects and the cost of the treatment.

The drug compositions of the present invention can be administered to an animal that has also undergone surgery as treatment for the cancer. In one embodiment of the present invention, the additional method of treatment is radiation therapy.

In a specific embodiment of the present invention, the composition of the present invention is administered concurrently with a chemotherapeutic agent or with radiation therapy. In another specific embodiment, the chemotherapeutic agent or radiation therapy is administered prior or subsequent to administration of a composition of the present invention, preferably at least an hour, five hours, 12 hours, a day, a week, a month, more preferably several months (e.g. up to three months), prior or subsequent to administration of a composition of the present invention. A chemotherapeutic agent can be administered over a series of sessions, any one or a combination of chemotherapeutic agents known in the art can be administered.

With respect to radiation, any radiation therapy protocol can be used depending upon the type of cancer to be treated. For example, but not by way of limitation, x-ray radiation can be administered; in particular, high-energy megavoltage (radiation of greater than 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

In the fourth aspect of the present invention, there is provided a kit comprising a comprising a tyrosine kinase inhibitor as defined above as an active ingredient and a 1,2,4-trioxane of formula (I) adjuvant as defined above or a pharmaceutically acceptable salt, ester, solvate, tautomer or stereoisomer thereof in an amount sufficient to enhance the activity of the tyrosine kinase inhibitor.

In one embodiment, the kit according to this aspect is for use in the treatment of cancer, and more preferably a cancer selected from lymphoma, breast cancer, leukemia, gastrointestinal tumors, nonsmall cell lung cancer, melanoma, renal carcinoma, multiple myeloma, kidney cancer, colon cancer, pancreatic cancer, lung cancer, ovarian cancer and prostate cancer.

As noted earlier, for both lymphoma and human breast cancer cell lines, for example it has been found that those of high proliferative capacity can be made significantly more sensitive (up to 4-fold) to tyrosine kinase inhibitors by use in combination with preferred synthetic trioxanes of the present invention as adjuvant. Moreover, highly malignant cancers, which are more difficult to treat, are more susceptible to the trioxane adjuvant effect than those of low malignancy.

Such enhancements and improvements could be compromised by the possible toxicity of the trioxane adjuvant. Toxicity might be a characteristic of a particular 1,2,4-trioxane, since neurotoxicity in rats and dogs has been reported for artemether, the semi-synthetic derivative of the naturally occurring 1,2,4-trioxane, artemisinin (T. G. Brewer, S. J. Grate, J. O. Peggins, P. J. Weina, J. M. Petras, B. S. Levine, M. H. Heiffer, and B. G. Schuster, *Ann. Trop. Med. Hyg.* 1994, 51, 251-259).

As a bellwether, the toxicity of trioxane T7 has been evaluated and compared with that of artemether in CD® rats following two weeks of oral administration (gavage) and intramuscular injection, respectively. Trioxane T7 was administered at doses of 0, 15, 30, and 60 mg/kg/day in Lipomul® emulsion, while artemether was dosed at 0, 10, 20, and 40 mg/kg/day. As a reminder, the structure of trioxane T7 is as follows:

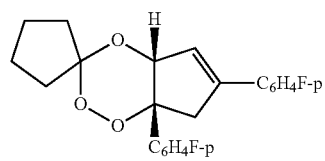

The primary toxic effects seen with trioxane T7 were normochromic, normocytic anemia at mid and high doses and it demonstrated hepatotoxicity at the high dose. No neurotoxicity was seen with trioxane T7. By contrast, artemether caused CNS excitability, neuronal chromatolysis, and gliosis in the brain stem. At mid-dose neurotoxic manifestations were observed, including hematoxicity and hepatotoxicity.

Finally, a dosage of 15 mg/kg/day for trioxane T7 was determined as the apparent no-effect dose in the aforementioned study. In addition, trioxane T7 was found to be negative in the *Salmonella/Escherichia coli* mutagenicity assay (Ames Test).

Further testing of trioxane T7 in a group of rats at 60 mg/kg/day resulted in no mortality, whereas artemether at a dose of 40 mg/kg/day killed most of the rats in the test.

EXAMPLES OF CANCER CELL INHIBITION IN VITRO

Example 1

To assess the in vitro sensitivity of poorly proliferating (MCF-7) and fast proliferating (MDA-468) breast cancer cell lines, cells were cultivated for 48 hours in the presence of 10 µM imatinib (a proprietary tyrosine kinase inhibitor) alone, with trioxane T7 (1 µM) alone, and 10 µM imatinib and 1 µM trioxane T7 together. The same experimental set-up was also utilized to test the synergistic capacity of trioxane T59 with imatinib. As a reminder, the structure of trioxane T59 is as follows:

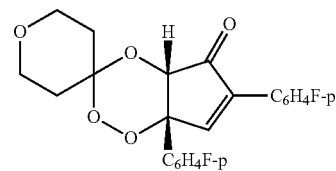

The controls included the naturally occurring TKI, genistein, and resveratrol, a non-peroxide, stilbene derivative. The test read-out was the Annexin V apoptosis assay kit from Becton-Dickinson, which detects the presence of the Annexin V protein on the surface of cells undergoing apoptosis and positivity toward propidium iodide for dead cells.

In the results presented, the values correspond to the percentage of dead cells (dead+apoptotic) and the baseline values for the vehicle controls are 13-18%. Synergy is expressed as moderate * or high **.

|  | MCF-7 | MDA-468 |
| --- | --- | --- |
| Imatinib 10 µM | 14.05% | 13.60% |
| Trioxane T7, 1 µM | 13.10% | 15.17% |
| Imatinib 10 µM + Trioxane T7, 1 µM | 17.00% | 48.27%** |
| Imatinib 10 µM | 14.15% | 13.16% |
| Trioxane T59, 1 µM | 19.00% | 13.70% |

-continued

|  | MCF-7 | MDA-468 |
|---|---|---|
| Imatinib 10 μM + Trioxane T59 1 μM | 27.10% * | 48.50%** |
| Genistein, 10 μM | 17.50% | 18.50% |
| Trioxane T7, 1 μM | 13.10% | 15.20% |
| Genistein, 10 μM + Trioxane T7, 1 μM | 15.40% | 48.10%** |
| Genistein, 10 μM | 17.50% | 18.50% |
| Resveratrol, 1 μM | 16.05% | 11.30% |
| Genistein, 10 μM + resveratrol, 1 μM | 17.50% | 18.50% |

These results show that the trioxanes T7 and T59 synergize well with imatinib when added to MDA cell cultures, but minimally when added to MCF-7 cultures (save for a moderate synergy between imatinib and trioxane T59). The naturally occurring TKI, genistein (an isoflavone extracted from soybeans), shows no synergy, either with trioxane T7 or resveratrol in MCF-7 cells. However, trioxane T7 synergizes well with genistein in MDA cells, whereas genistein and resveratrol synergize neither in MCF-7 nor in MDA cells, emphasizing the superior capacity of the synthetic trioxanes to modulate even the low activity genistein.

Example 2

To assess the in vitro sensitivity of a human follicular lymphoma cell line (DoHH2) and a human Burkitt's lymphoma cell line (Raji), cells were cultivated for 48 hours in the presence of 25 μM of dasatinib (a proprietary tyrosine kinase inhibitor effective on the non-receptor Lyn kinase) alone, or in the presence of trioxanes T16, T45, and BO7 all alone, each of which in concentrations of 1.0 and 10 μM. Next the cells were cultivated in the same way, but in the combined presence of dasatinib (25 μM) and the individual trioxanes T16, T45, and T7 in concentrations of 1.0 and 10 μM (see Tables below). As mentioned above, the Annexin V apoptosis assay was used to detect the Annexin V protein on cells undergoing apoptosis. Dead cells (post-apoptopic) were determined by positivity toward propidium iodide. The percentages of apoptopic, post-apoptopic cells, and their total are shown for each test. The baseline values for the vehicle controls are 13-18%. Synergy is noted as moderate (*), high (), or exceptionally high (*).

Human Follicular Lymphoma (DoHH2)

| Test Compound, In μM | Apoptopic Cells, in % | Post-apoptopic Cells, in % | Total Dead Cells, in % | Synergy in % |
|---|---|---|---|---|
| Dasatinib, 25 | 4.58 | 11.76 | 16.34 | — |
| Trioxane T16, 1.0 | 3.93 | 10.75 | 14.68 | — |
| Dasatinib, 25 + T16, 1.0 | 4.52 | 17.41 | 21.39 | * |
| Trioxane T16, 10 | 2.10 | 9.33 | 11.43 | — |
| Dasatinib, 25 + T16, 10 | 4.46 | 57.33 | 61.79 | *** |
| Trioxane T45, 10 | 2.15 | 9.55 | 11.7 | — |
| Dasatinib, 25 + T45, 10 | 3.64 | 55.37 | 59.01 | *** |
| Trioxane T7, 10 | 1.98 | 12.12 | 14.10 | — |
| Dasatinib, 25 + T7, 10 | 2.39 | 27.57 | 29.96 | ** |

Human Burkitt's Lymphoma (Raji)

| Test Compound, In μM | Apoptopic Cells, in % | Post-apoptopic Cells, in % | Total Dead Cells, in % | Synergy in % |
|---|---|---|---|---|
| Dasatinib, 25 | 7.9 | 15.18 | 23.15 | — |
| Trioxane T16, 1.0 | 3.39 | 7.08 | 10.47 | — |
| Dasatinib, 25 + T16, 1.0 | 6.68 | 18.13 | 24.81 | * |
| Trioxane T16, 10 | 2.98 | 14.3 | 17.58 | — |
| Dasatinib, 25 + T16, 10 | 4.27 | 41.47 | 45.69 | *** |
| Trioxane T7, 1.0 | 6.33 | 11.02 | 17.35 | — |
| Dasatinib, 25 + T7, 1.0 | 11.91 | 27.94 | 39.04 | *** |
| Trioxane T7, 10 | 5.91 | 15.66 | 20.57 | — |
| Dasatinib, 25 + T7, 10 | 11.18 | 28.08 | 39.26 | *** |

In the slowly proliferating DoHH2 cell line, dasatinib experiences strong synergy with trioxanes T16 and T45 at 10 μM, but only moderate synergy with T7 at 10 μM. In the fast proliferating Raji cell line, dasatinib shows strong synergy with 10 μM of trioxane T16, but none at the lower dose of 1.0 μM. In the same Raji line, trioxane T7 is powerfully synergistic both at 1.0 and 10 μM.

These results reveal that individual cell lines display specific patterns of sensitivity, possibly reflecting their different signaling modes.

The structures of the three trioxanes are shown below as a reminder.

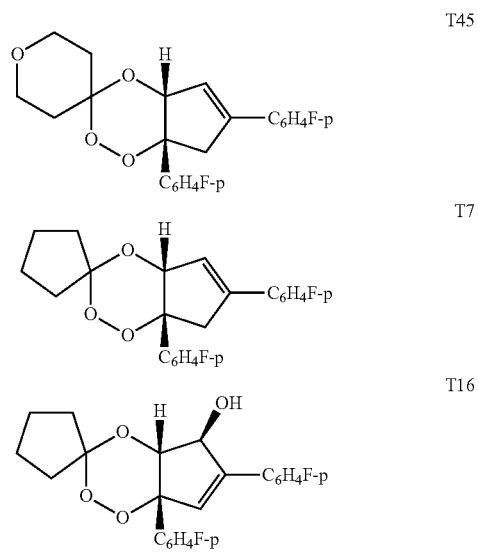

The invention claimed is:

1. A method of treating a patient having cancer that is treatable using a tyrosine kinase inhibitor (TKI), the method comprising administering to the patient a 1,2,4-trioxane of formula (I) or a pharmaceutically acceptable salt, ester, solvate, tautomer or stereoisomer thereof, as an adjuvant and a tyrosine kinase inhibitor (TKI) as an active ingredient to enhance the activity of said tyrosine kinase inhibitor:

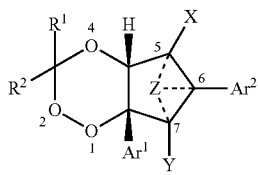

(I)

wherein
each of substituents $R^1$ and $R^2$, which can be the same or different, represents a linear or branched alkyl group having from 1 to 12 carbon atoms, a linear or branched alkenyl group having from 2 to 12 carbon atoms or a linear or branched alkynyl group having from 2 to 12 carbon atoms, each of which can optionally be substituted with one or more substituents chosen from substituents $R^x$, or $R^1$ and $R^2$ taken together with the carbon atom to which they are attached can form an alicyclic group having from 3 to 8 carbon atoms which may optionally be interrupted by one or more oxygen, sulphur or nitrogen atoms, wherein said alicyclic group may optionally be substituted with one or more substituents chosen from substituents $R^x$;

each of the substituents $Ar^1$ and $Ar^2$, which can be the same or different, represents an aromatic group selected from aryl groups having from 6 to 18 carbon atoms in one or more rings, and 5- to 14-membered heteroaryl groups having one or more rings, wherein said aryl group or said heteroaryl group may optionally be substituted with one or more substituents chosen from substituents $R^x$;

each of the substituents X and Y, which can be the same or different, represents a hydrogen atom or a functional group that contains oxygen, sulphur or nitrogen;

the substituent Z represents an epoxide oxygen atom attached to the 5,6 or 6,7 positions or a pair of electrons forming a double bond at the 5,6 or 6,7 positions; and said substituents $R^x$ are selected from the group consisting of $C_1$-$C_{12}$ alkyl groups which may be optionally substituted with at least one group $R^y$, $C_2$-$C_{12}$ alkenyl groups which may be optionally substituted with at least one group $R^y$, $C_2$-$C_{12}$ alkynyl groups which may be optionally substituted with at least one group $R^y$, halogen atoms, oxo groups, thio groups, cyano groups, nitro groups, $OR^y$, $OCOR^y$, $OCOOR^y$, $COR^y$, $COOR^y$, $OCONR^yR^z$, $CONR^yR^z$, $S(O)R^y$, $SO_2R^y$, $P(O)(R^y)OR^z$, $NR^yR^z$, $NR^yCOR^z$, $NR^yC(=O)NR^yR^z$, $NR^yC(=NR^y)NR^yR^z$, aryl groups having from 6 to 18 carbon atoms in one or more rings which may optionally be substituted with one or more substituents which may be the same or different selected from the group consisting of $R^y$, $OR^y$, $OCOR^y$, $OCOOR^y$, $NR^yR^z$, $NR^yCOR^z$ and $NR^yC(=NR^y)NR^yR^z$, aralkyl groups comprising an alkyl group having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R^y$, and where there is more than one optional substituent on any given group the optional substituents $R^y$ may be the same or different;

each $R^y$ and $R^z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl groups comprising a $C_1$-$C_{12}$ alkyl group that is substituted with a 5- to 14-membered unsaturated or saturated heterocyclic group having one or more rings and comprising at least one oxygen, nitrogen or sulphur atom in said ring(s), wherein the cancer is selected from the group consisting of: lymphoma, breast cancer, leukemia, gastrointestinal tumors, nonsmall cell lung cancer, melanoma, renal carcinoma, multiple myeloma, kidney cancer, colon cancer, pancreatic cancer, lung cancer, ovarian cancer, and prostate cancer.

2. A pharmaceutical composition comprising: (1) a tyrosine kinase inhibitor as an active ingredient, (2) a 1,2,4-trioxane of formula (I) or a pharmaceutically acceptable salt, ester, solvate, tautomer or stereoisomer thereof as an adjuvant, in an amount sufficient to enhance the activity of the tyrosine kinase inhibitor, and (3) a pharmaceutically acceptable carrier:

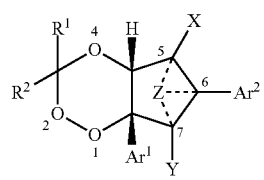

(I)

wherein
each of substituents $R^1$ and $R^2$, which can be the same or different, represents a linear or branched alkyl group having from 1 to 12 carbon atoms, a linear or branched alkenyl group having from 2 to 12 carbon atoms or a linear or branched alkynyl group having from 2 to 12 carbon atoms, each of which can optionally be substituted with one or more substituents chosen from substituents $R^x$, or $R^1$ and $R^2$ taken together with the carbon atom to which they are attached can form an alicyclic group having from 3 to 8 carbon atoms which may optionally be interrupted by one or more oxygen, sulphur or nitrogen atoms, wherein said alicyclic group may optionally be substituted with one or more substituents chosen from substituents $R^x$;

each of the substituents $Ar^1$ and $Ar^2$, which can be the same or different, represents an aromatic group selected from aryl groups having from 6 to 18 carbon atoms in one or more rings, and 5- to 14-membered heteroaryl groups having one or more rings, wherein said aryl group or said heteroaryl group may optionally be substituted with one or more substituents chosen from substituents $R^x$;

each of the substituents X and Y, which can be the same or different, represents a hydrogen atom or a functional group that contains oxygen, sulphur or nitrogen;

the substituent Z represents an epoxide oxygen atom attached to the 5,6 or 6,7 positions or a pair of electrons forming a double bond at the 5,6 or 6,7 positions; and said substituents $R^x$ are selected from the group consisting of $C_1$-$C_{12}$ alkyl groups which may be optionally substituted with at least one group $R^y$, $C_2$-$C_{12}$ alkenyl groups which may be optionally substituted with at least one group $R^y$, $C_2$-$C_{12}$ alkynyl groups which may be optionally substituted with at least one group $R^y$, halogen atoms, oxo groups, thio groups, cyano groups, nitro groups, $OR^y$, $OCOR^y$, $OCOOR^y$, $COR^y$, $COOR^y$, $OCONR^yR^z$, $CONR^yR^z$, $S(O)R^y$, $SO_2R^y$, $P(O)(R^y)OR^z$, $NR^yR^z$, $NR^yCOR^z$, $NR^yC(=O)NR^yR^z$, $NR^yC(=NR^y)NR^yR^z$, aryl groups having from 6 to 18 carbon atoms in one or more rings which may optionally be substituted with one or more substituents which may be the same or different selected from the group consisting of $R^y$, $OR^y$, $OCOR^y$, $OCOOR^y$, $NR^yR^z$, $NR^yCOR^z$ and $NR^yC(=NR^y)NR^yR^z$, aralkyl groups comprising an alkyl group having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R^y$, and where there is more than one optional substituent on any given group the optional substituents $R^y$ may be the same or different;

each $R^y$ and $R^z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl groups comprising a $C_1$-$C_{12}$ alkyl group that is substituted with a 5- to 14-membered unsaturated or saturated heterocyclic group having one or more rings and comprising at least one oxygen, nitrogen or sulphur atom in said ring(s).

3. The pharmaceutical composition according to claim 2, wherein said pharmaceutical composition is formulated such that said 1,2,4-trioxane of formula (I) or a pharmaceutically acceptable salt, ester, solvate, tautomer or stereoisomer thereof and said TKI can be either administered simultaneously or stepwise.

4. The pharmaceutical composition according to claim 2, wherein each of substituents $R^1$ and $R^2$, which can be the same or different, represents a linear or branched alkyl group having from 1 to 6 carbon atoms, a linear or branched alkenyl group having from 2 to 6 carbon atoms or a linear or branched alkynyl group having from 2 to 6 carbon atoms, each of which can optionally be substituted with one or more substituents chosen from substituents $R^x$, or $R^1$ and $R^2$ taken together with the carbon atom to which they are attached can form an alicyclic group having from 4 to 6 carbon atoms which may optionally be interrupted by one or more oxygen, sulphur or nitrogen atoms, wherein said alicyclic group may optionally be substituted with one or more substituents chosen from substituents $R^x$.

5. The pharmaceutical composition according to claim 2, wherein each of substituents $R^1$ and $R^2$, which can be the same or different, represents a methyl, ethyl, isopropyl, t-butyl, vinyl or ethynyl group which can optionally be substituted with one or more substituents chosen from $R^{x'}$, or $R^1$ and $R^2$ taken together with the carbon atom to which they are attached can form an alicyclic group having 5 or 6 carbon atoms which may optionally be interrupted by one or more oxygen atoms, wherein said alicyclic group may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms.

6. The pharmaceutical composition according to claim 2, wherein $Ar^1$ and $Ar^2$, which can be the same or different, represents an aromatic group selected from aryl groups having from 6 to 12 carbon atoms in one or more rings, and 5- to 14-membered heteroaryl groups having one or more rings, wherein said aryl group or said heteroaryl group may optionally be substituted with one or more substituents chosen from substituents $R^x$.

7. The pharmaceutical composition according to claim 2, wherein $Ar^1$ and $Ar^2$, which can be the same or different, represents a group selected from a phenyl group, a pyridine group, a pyrimidinyl group, a furyl group, a pyrrolyl group and a thienyl group, wherein said groups may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms.

8. The pharmaceutical composition according to claim 2, wherein each of the substituents X and Y, which can be the same or different, represents a group selected from a hydrogen atom or a functional group that contains oxygen, sulphur or nitrogen selected from an oxo group, a hydroxyl group, a hydroperoxy group, an alkoxy group having from 1 to 6 carbon atoms, a group of formula $OCOR^y$ wherein $R^y$ is an alkyl group having from 1 to 6 carbon atoms, a group of formula $OCOOR^y$ wherein $R^y$ is an alkyl group having from 1 to 6 carbon atoms, a group of formula $=NR^y$ wherein $R^y$ is a hydrogen atom or an alkyl group having from 1 to 6 carbon atoms, a group of formula $NR^yR^z$ wherein each of $R^y$ and $R^z$, which can be the same or different, can be a hydrogen atom or an alkyl group having from 1 to 6 carbon atoms, a group of formula $NR^yCOR^z$, wherein each of $R^y$ and $R^z$ can the same or different and is hydrogen or an alkyl group having from 1 to 6 carbon atoms, a nitro group, a thione group, a thiol group, a disulfane group, a group of formula $S(O)R^y$ wherein $R^y$ is a hydrogen atom or an alkyl group having from 1 to 6 carbon atoms and a group of formula $SO_2R$ wherein $R^y$ is a hydrogen atom or an alkyl group having from 1 to 6 carbon atoms.

9. The pharmaceutical composition according to claim 2, wherein each of the substituents X and Y, which can be the same or different, represents a substituent selected from hydrogen atom, an oxo group, a hydroxyl group, a hydroperoxy group, a group of formula $OCOOR^y$ wherein $R^y$ is an alkyl group having from 1 to 6 carbon atoms, an amino group, an imine group, a thione group and a thiol group.

10. The pharmaceutical composition according to claim 2, wherein the 1,2,4-trioxane of formula (I) is selected from the following group:

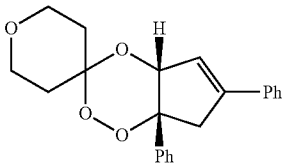

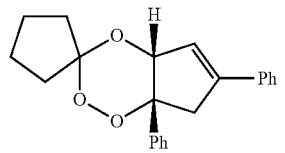

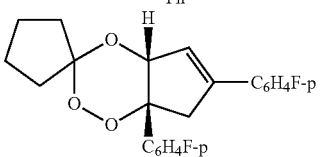

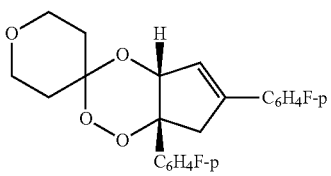

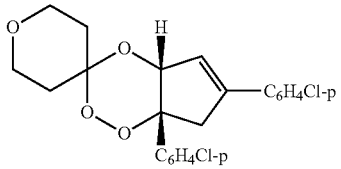

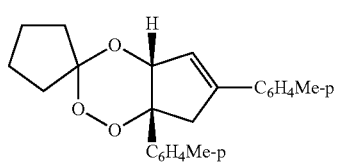

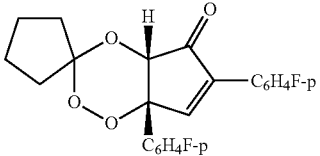

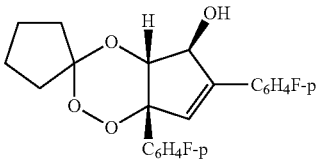

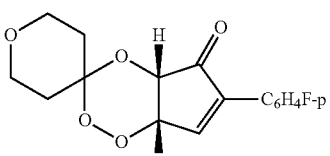

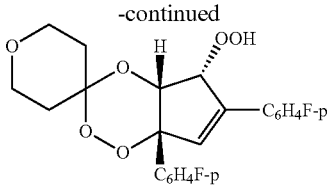

or a pharmaceutically acceptable salt, ester, solvate, tautomer or stereoisomer thereof.

11. The pharmaceutical composition according to claim 2, wherein the tyrosine kinase inhibitor is an inhibitor of a kinase selected from an epidermal growth factor receptor (EGFR), a platelet derived growth factor (PDGF), bcr-abl, c-KIT kinase, FLT kinase, a platelet derived growth factor (PDGFR), a vascular endothelial growth factor (VEGFR) and Src-family non-receptor kinases.

12. The pharmaceutical composition according to claims 11, wherein the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol.

13. The pharmaceutical composition according to claim 2, wherein the 1,2,4-trioxane of formula (I) adjuvant or a pharmaceutically acceptable salt, ester, solvate, tautomer or stereoisomer thereof is as defined below:

each of substituents $R^1$ and $R^2$, which can be the same or different, represents a linear or branched alkyl group having from 1 to 6 carbon atoms, a linear or branched alkenyl group having from 2 to 6 carbon atoms or a linear or branched alkynyl group having from 2 to 6 carbon atoms, each of which can optionally be substituted with one or more substituents chosen from substituents $R^x$, or $R^1$ and $R^2$ taken together with the carbon atom to which they are attached can form an alicyclic group having from 4 to 6 carbon atoms which may optionally be interrupted by one or more oxygen, sulphur or nitrogen atoms, wherein said alicyclic group may optionally be substituted with one or more substituents chosen from substituents $R^x$;

$Ar^1$ and $Ar^2$, which can be the same or different, represents an aromatic group selected from aryl groups having from 6 to 12 carbon atoms in one or more rings, and 5- to 8-membered heteroaryl groups having one or more rings, wherein said aryl group or said heteroaryl group may optionally be substituted with one or more substituents chosen from substituents $R^x$;

each of the substituents X and Y, which can be the same or different, represents a substituent selected from a hydrogen atom or a functional group that contains oxygen, sulphur or nitrogen selected from an oxo group, a hydroxyl group, a hydroperoxy group, an alkoxy group having from 1 to 6 carbon atoms, a group of formula $OCOR^y$ wherein $R^y$ is an alkyl group having from 1 to 6 carbon atoms, a group of formula $OCOOR^y$ wherein $R^y$ is an alkyl group having from 1 to 6 carbon atoms, a group of formula $=NR^y$ wherein $R^y$ is a hydrogen atom or an alkyl group having from 1 to 6 carbon atoms, a group of formula $NR^yR^z$ wherein each of $R^y$ and $R^z$, which can be the same or different, can be a hydrogen atom or an alkyl group having from 1 to 6 carbon atoms, a group of formula $NR^yCOR^z$, wherein each of $R^y$ and $R^z$ can the same or different and is hydrogen or an alkyl group having from 1 to 6 carbon atoms, a nitro group, a thione group, a thiol group, a disulfane group, a group of formula S(O)R$^y$ wherein R$^y$ is a hydrogen atom or an alkyl group having from 1 to 6 carbon atoms and a group of formula SO$_2$R wherein R$^y$ is a hydrogen atom or an alkyl group having from 1 to 6 carbon atoms; and the substituent Z represents an epoxide oxygen atom attached to the 5,6 or 6,7 positions or a pair of electrons forming a double bond at the 5,6 or 6,7 positions; and the tyrosine kinase inhibitor is an inhibitor of a kinase selected from an epidermal growth factor receptor (EGFR), platelet derived growth factor (PDGF), bcr-abl, c-KIT kinase, FLT kinase, platelet derived growth factor (PDGFR), vascular endothelial growth factor (VEGFR) and Src-family non-receptor kinases.

14. The pharmaceutical composition according to claim 2, wherein the 1,2,4-trioxane of formula (I) adjuvant or pharmaceutically acceptable salt, ester, solvate, tautomer or stereoisomer thereof is as defined below:

R$^1$ and R$^2$, which can be the same or different, represents a methyl, ethyl, isopropyl, t-butyl, vinyl or ethynyl group which can optionally be substituted with one or more substituents chosen from R$^{x'}$, or R$^1$ and R$^2$ taken together with the carbon atom to which they are attached can form an alicyclic group having 5 or 6 carbon atoms which may optionally be interrupted by one or more oxygen atoms, wherein said alicyclic group may optionally be substituted with one or more substituents chosen from substituents R$^{x'}$, wherein R$^{x'}$ is selected from the group consisting of halogen, alkoxy groups having from 1 to 6 carbon atoms, groups of formula NR$^{y'}$R$^{z'}$ wherein each of R$^{y'}$ and R$^{z'}$ is the same or different and is hydrogen or an alkyl group having from 1 to 6 carbon atoms, cyano groups, nitro groups, hydroxyl groups, groups of formula OCOOR$^{y''}$ and groups of formula OCOR$^{y''}$ wherein R$^{y''}$ is an alkyl group having from 1 to 6 carbon atoms;

Ar$^1$ and Ar$^2$, which can be the same or different, represents a substituent selected from a phenyl group, a pyridine group, a pyrimidinyl group, a furyl group, a pyrrolyl group and a thienyl group, wherein said groups may optionally be substituted with one or more substituents chosen from substituents R$^{x'}$, wherein R$^{x'}$ is selected from the group consisting of halogen, alkoxy groups having from 1 to 6 carbon atoms, groups of formula NR$^{y'}$R$^{z'}$ wherein each of R$^{y'}$ and R$^{z'}$ is the same or different and is hydrogen or an alkyl group having from 1 to 6 carbon atoms, cyano groups, nitro groups, hydroxyl groups, groups of formula OCOOR$^{y''}$ and groups of formula OCOR$^{y''}$ wherein R$^{y''}$ is an alkyl group having from 1 to 6 carbon atoms;

each of the substituents X and Y, which can be the same or different, represents a substituent selected from hydrogen atom, an oxo group, a hydroxyl group, a hydroperoxy group, a group of formula OCOOR$^y$ wherein R$^y$ is an alkyl group having from 1 to 6 carbon atoms, an amino group, an imine group, a thione group and a thiol group; and the substituent Z represents a pair of electrons forming a double bond at the 5,6 or 6,7 positions; and the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol.

15. The pharmaceutical composition according to claim 2, wherein:

the 1,2,4-trioxane of formula (I) adjuvant is selected from the following compounds or a pharmaceutically acceptable salt, ester, solvate, tautomer or stereoisomer thereof

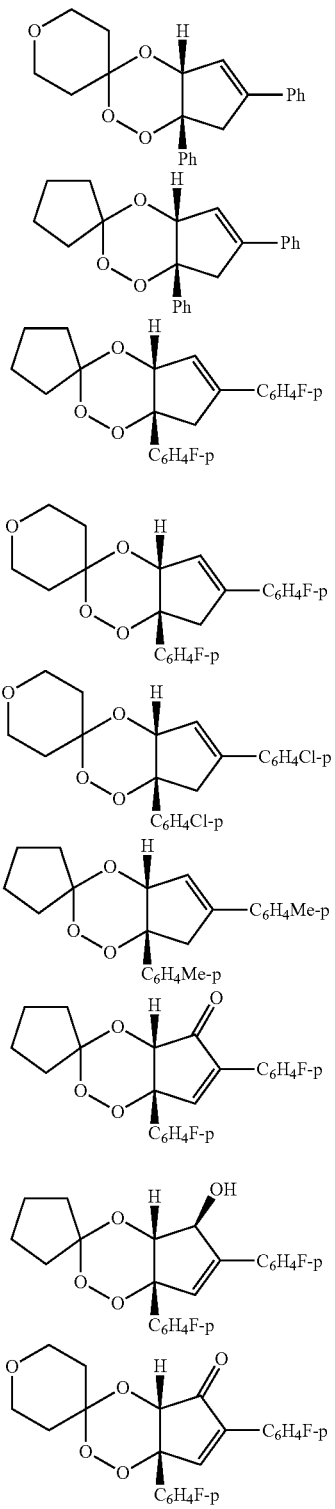

-continued

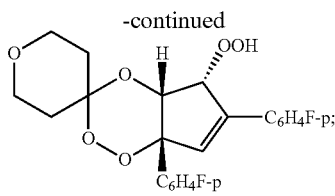

and
the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol.

16. The pharmaceutical composition according to claim 2, wherein the 1,2,4-trioxane of formula (I) is selected from the following compounds or a pharmaceutically acceptable salt, ester, solvate, tautomer or stereoisomer thereof:

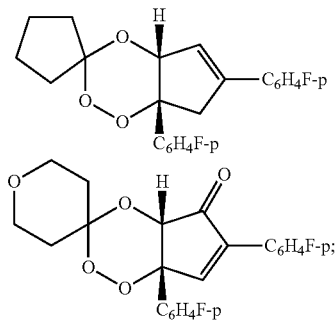

and
the tyrosine kinase inhibitor is selected from imatinib and genistein.

17. The pharmaceutical composition according to claim 2, wherein the molar ratio of the tyrosine kinase inhibitor active ingredient to the 1,2,4-trioxane of formula (I) or a pharmaceutically acceptable salt, ester, solvate, tautomer or stereoisomer thereof is from 50:1 to 1:1.

18. A kit comprising (1) a tyrosine kinase inhibitor as defined in claim 17 as an active ingredient, and (2) a 1,2,4-trioxane of formula (I) or a pharmaceutically acceptable salt, ester, solvate, tautomer or stereoisomer thereof as defined in claim 2 as an adjuvant in an amount sufficient to enhance the activity of the tyrosine kinase inhibitor.

19. The method according to claim 1, wherein said 1,2,4-trioxane of formula (I) or pharmaceutically acceptable salt, ester, solvate, tautomer or stereoisomer thereof, and said TKI are administered either simultaneously or stepwise.

20. The method according to claim 1, wherein each of substituents $R^1$ and $R^2$, which can be the same or different, represents a linear or branched alkyl group having from 1 to 6 carbon atoms, a linear or branched alkenyl group having from 2 to 6 carbon atoms or a linear or branched alkynyl group having from 2 to 6 carbon atoms, each of which can optionally be substituted with one or more substituents chosen from substituents $R^x$, or $R^1$ and $R^2$ taken together with the carbon atom to which they are attached can form an alicyclic group having from 4 to 6 carbon atoms which may optionally be interrupted by one or more oxygen, sulphur or nitrogen atoms, wherein said alicyclic group may optionally be substituted with one or more substituents chosen from substituents $R^x$.

21. The method according to claim 1, wherein each of substituents $R^1$ and $R^2$, which can be the same or different, represents a methyl, ethyl, isopropyl, t-butyl, vinyl or ethynyl group which can optionally be substituted with one or more substituents chosen from $R^{x'}$, or $R^1$ and $R^2$ taken together with the carbon atom to which they are attached can form an alicyclic group having 5 or 6 carbon atoms which may optionally be interrupted by one or more oxygen atoms, wherein said alicyclic group may optionally be substituted with one or more substituents chosen from substituents $R^{x'}$,
wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms.

22. The method according to claim 1, wherein $Ar^1$ and $Ar^2$, which can be the same or different, represents an aromatic group selected from aryl groups having from 6 to 12 carbon atoms in one or more rings, and 5- to 8-membered heteroaryl groups having one or more rings, wherein said aryl group or said heteroaryl group may optionally be substituted with one or more substituents chosen from substituents $R^x$.

23. The method according to claim 1, wherein $Ar^1$ and $Ar^2$, which can be the same or different, represents a group selected from a phenyl group, a pyridine group, a pyrimidinyl group, a furyl group, a pyrrolyl group and a thienyl group, wherein said groups may optionally be substituted with one or more substituents chosen from substituents $R^{x'}$,
wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms.

24. The method according to claim 1, wherein each of the substituents X and Y, which can be the same or different, represents a group selected from a hydrogen atom or a functional group that contains oxygen, sulphur or nitrogen selected from an oxo group, a hydroxyl group, a hydroperoxy group, an alkoxy group having from 1 to 6 carbon atoms, a group of formula $OCOR^y$ wherein $R^y$ is an alkyl group having from 1 to 6 carbon atoms, a group of formula $OCOOR^y$ wherein $R^y$ is an alkyl group having from 1 to 6 carbon atoms, a group of formula $=NR^y$ wherein $R^y$ is a hydrogen atom or an alkyl group having from 1 to 6 carbon atoms, a group of formula $NR^yR^z$ wherein each of $R^y$ and $R^z$, which can be the same or different, can be a hydrogen atom or an alkyl group having from 1 to 6 carbon atoms, a group of formula $NR^yCOR^z$, wherein each of $R^y$ and $R^z$ can the same or different and is hydrogen or an alkyl group having from 1 to 6 carbon atoms, a nitro group, a thione group, a thiol group, a disulfane group, a group of formula $S(O)R^y$ wherein $R^y$ is a hydrogen atom or an alkyl group having from 1 to 6 carbon atoms and a group of formula $SO_2R$ wherein $R^y$ is a hydrogen atom or an alkyl group having from 1 to 6 carbon atoms.

25. The method according to claim 1, wherein each of the substituents X and Y, which can be the same or different, represents a substituent selected from hydrogen atom, an oxo group, a hydroxyl group, a hydroperoxy group, a group of formula OCOOR$^y$ wherein R$^y$ is an alkyl group having from 1 to 6 carbon atoms, an amino group, an imine group, a thione group and a thiol group.

26. The method according to claim 1, wherein the 1,2,4-trioxane of formula (I) is:

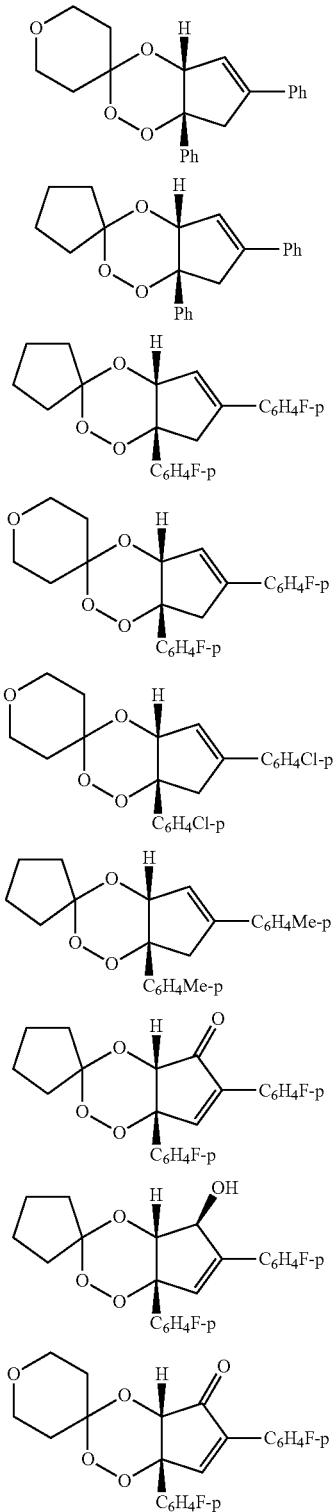

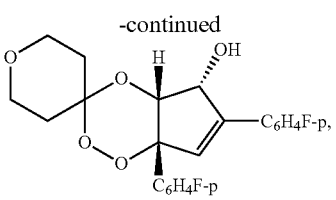

or pharmaceutically acceptable salt, ester, solvate, tautomer or stereoisomer thereof.

27. The method according to claim 1, wherein the tyrosine kinase inhibitor is an inhibitor of a kinase selected from an epidermal growth factor receptor (EGFR), a platelet derived growth factor (PDGF), bcr-abl, c-KIT kinase, FLT kinase, a platelet derived growth factor (PDGFR), a vascular endothelial growth factor (VEGFR) and Src-family non-receptor kinases.

28. The method according to claim 27, wherein the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol.

29. The method according to claim 1, wherein each of substituents R$^1$ and R$^2$, which can be the same or different, represents a linear or branched alkyl group having from 1 to 6 carbon atoms, a linear or branched alkenyl group having from 2 to 6 carbon atoms or a linear or branched alkynyl group having from 2 to 6 carbon atoms, each of which can optionally be substituted with one or more substituents chosen from substituents R$^x$, or R$^1$ and R$^2$ taken together with the carbon atom to which they are attached can form an alicyclic group having from 4 to 6 carbon atoms which may optionally be interrupted by one or more oxygen, sulphur or nitrogen atoms, wherein said alicyclic group may optionally be substituted with one or more substituents chosen from substituents R$^x$;

Ar$^1$ and Ar$^2$, which can be the same or different, represents an aromatic group selected from aryl groups having from 6 to 12 carbon atoms in one or more rings, and 5- to 8-membered heteroaryl groups having one or more rings, wherein said aryl group or said heteroaryl group may optionally be substituted with one or more substituents chosen from substituents R$^x$;

each of the substituents X and Y, which can be the same or different, represents a substituent selected from a hydrogen atom or a functional group that contains oxygen, sulphur or nitrogen selected from an oxo group, a hydroxyl group, a hydroperoxy group, an alkoxy group having from 1 to 6 carbon atoms, a group of formula OCOR$^y$ wherein R$^y$ is an alkyl group having from 1 to 6 carbon atoms, a group of formula OCOOR$^y$ wherein R$^y$ is an alkyl group having from 1 to 6 carbon atoms, a group of formula =NR$^y$ wherein R$^y$ is a hydrogen atom or an alkyl group having from 1 to 6 carbon atoms, a group of formula NR$^y$R$^z$ wherein each of R$^y$ and R$^z$, which can be the same or different, can be a hydrogen atom or an alkyl group having from 1 to 6 carbon atoms, a group of formula NR$^y$COR$^z$, wherein each of R$^y$ and R$^z$ can the same or different and is hydrogen or an alkyl group having from 1 to 6 carbon atoms, a nitro group, a thione group, a thiol group, a disulfane group, a group of formula S(O)R$^y$ wherein R$^y$ is a hydrogen atom or an alkyl group having from 1 to 6 carbon atoms and a group of formula $SO_2R$ wherein $R^y$ is a hydrogen atom or an alkyl group having from 1 to 6 carbon atoms;

the substituent Z represents an epoxide oxygen atom attached to the 5,6 or 6,7 positions or a pair of electrons forming a double bond at the 5,6 or 6,7 positions; and the tyrosine kinase inhibitor is an inhibitor of a kinase selected from an epidermal growth factor receptor (EGFR), platelet derived growth factor (PDGF), bcr-abl, c-KIT kinase, FLT kinase, platelet derived growth factor (PDGFR), vascular endothelial growth factor (VEGFR) and Src-family non-receptor kinases.

30. The method according to claim 1, wherein:

$R^1$ and $R^2$, which can be the same or different, represents a methyl, ethyl, isopropyl, t-butyl, vinyl or ethynyl group which can optionally be substituted with one or more substituents chosen from $R^{x'}$, or $R^1$ and $R^2$ taken together with the carbon atom to which they are attached can form an alicyclic group having 5 or 6 carbon atoms which may optionally be interrupted by one or more oxygen atoms, wherein said alicyclic group may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms;

$Ar^1$ and $Ar^2$, which can be the same or different, represents a substituent selected from a phenyl group, a pyridine group, a pyrimidinyl group, a furyl group, a pyrrolyl group and a thienyl group, wherein said groups may optionally be substituted with one or more substituents chosen from substituents $R^{x'}$, wherein $R^{x'}$ is selected from the group consisting of halogen, alkoxy groups having from 1 to 6 carbon atoms, groups of formula $NR^{y'}R^{z'}$ wherein each of $R^{y'}$ and $R^{z'}$ is the same or different and is hydrogen or an alkyl group having from 1 to 6 carbon atoms, cyano groups, nitro groups, hydroxyl groups, groups of formula $OCOOR^{y''}$ and groups of formula $OCOR^{y''}$ wherein $R^{y''}$ is an alkyl group having from 1 to 6 carbon atoms;

each of the substituents X and Y, which can be the same or different, represents a substituent selected from hydrogen atom, an oxo group, a hydroxyl group, a hydroperoxy group, a group of formula $OCOOR^y$ wherein $R^y$ is an alkyl group having from 1 to 6 carbon atoms, an amino group, an imine group, a thione group and a thiol group;

the substituent Z represents a pair of electrons forming a double bond at the 5,6 or 6,7 positions; and the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol.

31. The method according to claim 1, wherein:

the 1,2,4-trioxane of formula (I) is selected from the following compounds or a pharmaceutically acceptable salt, ester, solvate, tautomer or stereoisomer thereof

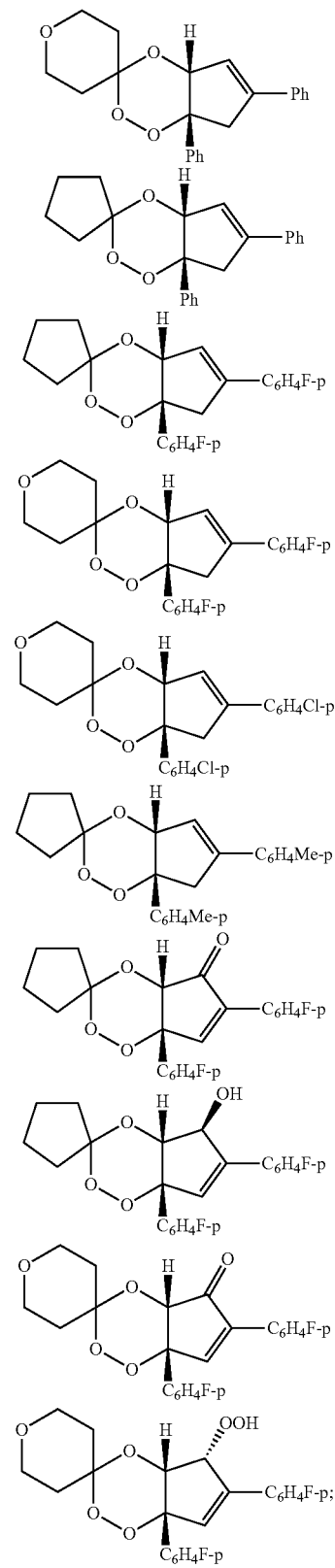

and the tyrosine kinase inhibitor is selected from imatinib, gefitinib, erlotinib, lapatinib, canertinib, vatalanib, sorafenib, axitinib, dasatinib, nilotinib, pazopanib, sunitinib, semaxinib, bosutinib, cabozatinib, crizotinib, masitinib, neratinib B, regorafenib, vandetanib, genistein, emodin and radiciol.

32. The method according to claim 31, wherein the 1,2,4-trioxane of formula (I) is selected from the following compounds or pharmaceutically acceptable salt, ester, solvate, tautomer or stereoisomer thereof:

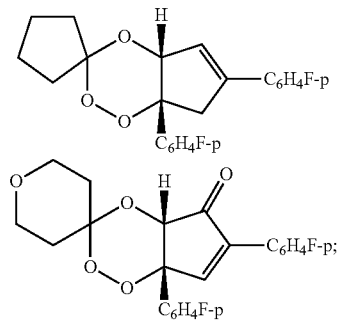

and the tyrosine kinase inhibitor is selected from imatinib and genistein.

33. The method according to claim 1, wherein the molar ratio of the tyrosine kinase inhibitor to the 1,2,4-trioxane of formula (I) or pharmaceutically acceptable salt, ester, solvate, tautomer or stereoisomer thereof is from 50:1 to 1:1.

34. The method according to claim 1, wherein the molar ratio of the tyrosine kinase inhibitor to the 1,2,4-trioxane of formula (I) or pharmaceutically acceptable salt, ester, solvate, tautomer or stereoisomer thereof is from 20:1 to 1:1.

35. The method according to claim 1, wherein the molar ratio of the tyrosine kinase inhibitor to the 1,2,4-trioxane of formula (I) or pharmaceutically acceptable salt, ester, solvate, tautomer or stereoisomer thereof is from 15:1 to 5:1.

36. The pharmaceutical composition according to claim 2, wherein the molar ratio of the tyrosine kinase inhibitor active ingredient to the 1,2,4-trioxane of formula (I) or a pharmaceutically acceptable salt, ester, solvate, tautomer or stereoisomer thereof is from 20:1 to 1:1.

37. The pharmaceutical composition according to claim 2, wherein the molar ratio of the tyrosine kinase inhibitor active ingredient to the 1,2,4-trioxane of formula (I) or a pharmaceutically acceptable salt, ester, solvate, tautomer or stereoisomer thereof is from 15:1 to 5:1.

38. A method of treating a patient having cancer that is treatable using a tyrosine kinase inhibitor (TKI), the method comprising administering to the patient a pharmaceutical composition as defined in claim 2, wherein the cancer is selected from the group consisting of: lymphoma, breast cancer, leukemia, gastrointestinal tumors, nonsmall cell lung cancer, melanoma, renal carcinoma, multiple myeloma, kidney cancer, colon cancer, pancreatic cancer, lung cancer, ovarian cancer, and prostate cancer.

* * * * *

UNITED STATES PATENT AND TRADEMARK OFFICE
CERTIFICATE OF CORRECTION

PATENT NO. : 9,763,915 B2  
APPLICATION NO. : 15/041198  
DATED : September 19, 2017  
INVENTOR(S) : Charles William Jefford et al.

Page 1 of 1

It is certified that error appears in the above-identified patent and that said Letters Patent is hereby corrected as shown below:

In the Claims

In Claim 18, Column 43, Line 45, please replace "claim 17" with --claim 2--;

In Claim 26, Column 46, Lines 1-10, please replace the compound structure

" 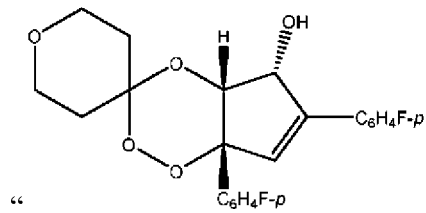 " with the following compound structure

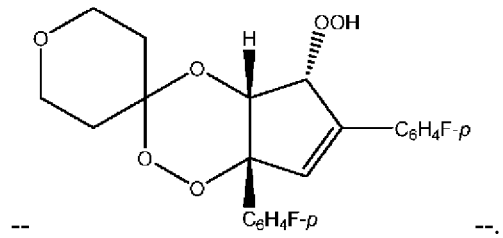 --.

Signed and Sealed this  
Seventh Day of November, 2017

Joseph Matal  
*Performing the Functions and Duties of the  
Under Secretary of Commerce for Intellectual Property and  
Director of the United States Patent and Trademark Office*